United States Patent
Tse-Dinh et al.

(10) Patent No.: US 11,839,621 B2
(45) Date of Patent: *Dec. 12, 2023

(54) TREATMENTS OF PROSTATE CANCER

(71) Applicants: Yuk-Ching Tse-Dinh, Coral Gables, FL (US); Yuan Liu, Miami, FL (US); Irina Agoulnik, Doral, FL (US)

(72) Inventors: Yuk-Ching Tse-Dinh, Coral Gables, FL (US); Yuan Liu, Miami, FL (US); Irina Agoulnik, Doral, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/048,504

(22) Filed: Oct. 21, 2022

(65) Prior Publication Data

US 2023/0226090 A1 Jul. 20, 2023

Related U.S. Application Data

(63) Continuation of application No. 17/697,306, filed on Mar. 17, 2022, now Pat. No. 11,478,496, which is a continuation of application No. 16/751,696, filed on Jan. 24, 2020, now Pat. No. 11,304,969.

(51) Int. Cl.
| | |
|---|---|
| *A61K 31/7048* | (2006.01) |
| *A61P 35/00* | (2006.01) |
| *A61K 45/06* | (2006.01) |
| *A61K 31/546* | (2006.01) |
| *A61K 31/4365* | (2006.01) |
| *A61K 31/593* | (2006.01) |

(52) U.S. Cl.
CPC .......... *A61K 31/7048* (2013.01); *A61P 35/00* (2018.01); *A61K 31/4365* (2013.01); *A61K 31/546* (2013.01); *A61K 31/593* (2013.01); *A61K 45/06* (2013.01)

(58) Field of Classification Search
CPC .............. A61K 31/7048; A61K 31/593; A61K 31/546; A61K 31/4365; A61P 35/00
See application file for complete search history.

(56) References Cited

U.S. PATENT DOCUMENTS

| | | | |
|---|---|---|---|
| 11,304,969 B2* | 4/2022 | Tse-Dinh | A61P 35/00 |
| 11,478,496 B2* | 10/2022 | Tse-Dinh | A61P 35/00 |
| 2017/0304387 A1* | 10/2017 | Chen | A61K 31/505 |

OTHER PUBLICATIONS

Sintov (Investigational New Drugs (2013) 31:247-255).*
Kong (Journal of Biological Chemistry; 2018, 293(37), 14328-14341).*
Bergoglio, V., et al., "Enhanced expression and activity of DNA polymerase β in human ovarian tumor cells: impact on sensitivity towards antitumor agents," Oncogene, 2001, 20(43): 6181-6187.
Evans, J.R., et al., "Patient-level DNA damage and repair pathway profiles and prognosis after prostatectomy for high-risk prostate cancer," JAMA oncology, 2016, 2(4): 471-480.
Kong, Yifan et al., "Inhibition of cholesterol biosynthesis overcomes enzalutamide resistance in castration-resistant prostate cancer (CRPC)," J. Biol. Chem. (2018) 293(37):14328-14341.
Sintov, Ammon C. et al., "Inhibition of cancer growth and induction of apoptosis by BGP-13 and BGP-15, new calcipotriene-derived vitamin D3 analogs, in-vitro and in-vivo studies," Invest New Drugs (2013) 31:247-255.
Sun, D., et al., "Elevated Expression of DNA Ligase I in Human Cancers," Clinical Cancer Research, Dec. 2001, 7(12): 4143-4148.
Vasquez, J.L., et al., "Inhibition of base excision repair by natamycin suppresses prostate cancer cell proliferation," Biochimie, 2020, 168: 241-250.
Wilson, S.H., et al., "Base excision repair and design of small molecule inhibitors of human DNA polymerase β," Cell. Mol. Life Sci., 2010, 67(21): 3633-3647.
Zhu, Zhu et al. "Doxycycline synergizes with doxorubicin to inhibit the proliferation of castration-resistant prostate cancer cells," Acta Biochim Biophys Sin (2017), 49(11):999-1007.

* cited by examiner

*Primary Examiner* — Pancham Bakshi
(74) *Attorney, Agent, or Firm* — SALIWANCHIK, LLOYD & EISENSCHENK

(57) ABSTRACT

The present invention provides compounds, compositions, and methods for the treatment of prostate cancers, preferably, advanced prostate cancers. The subject invention also provides compounds, compositions, and methods for preventing/slowing down/reducing the progress and proliferation of prostate cancer cells. The subject invention further provides compounds, compositions, and methods for inhibiting DNA repair within cancer cells to slow tumor growth, preferably, by inhibiting BER capacity, including pol β and LIG I.

18 Claims, 9 Drawing Sheets

Specification includes a Sequence Listing.

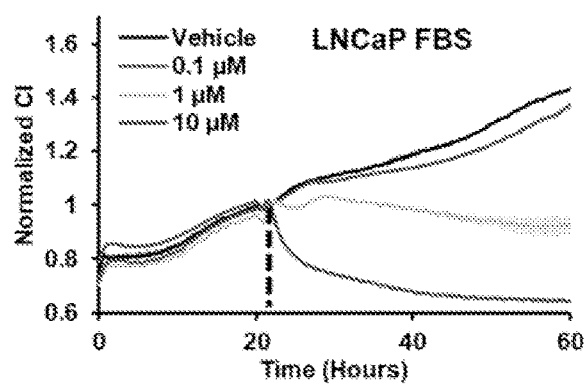 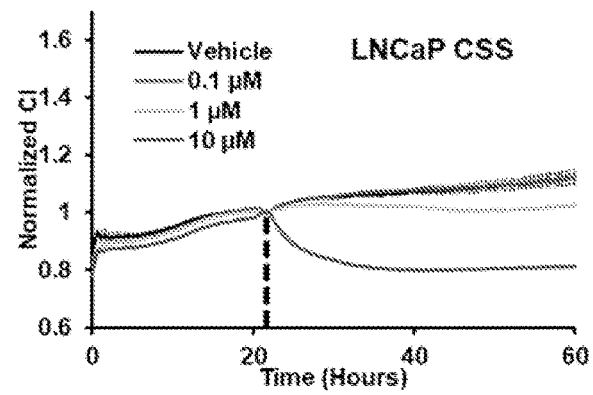
FIG. 7A    FIG. 7B
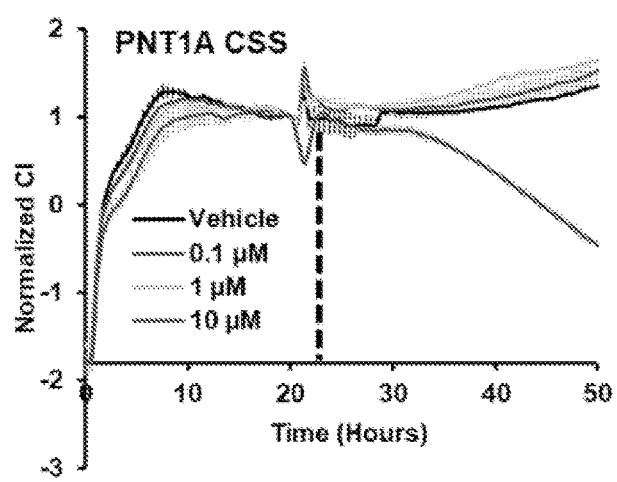 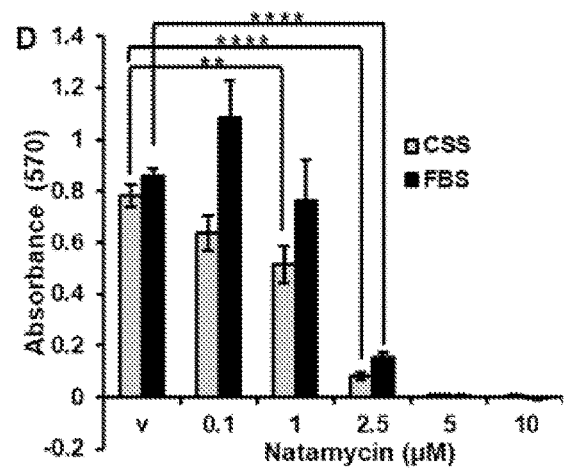
FIG. 7C    FIG. 7D

SEQUENCE LISTING

```
Sequence total quantity: 2
SEQ ID NO: 1              moltype = DNA  length = 48
FEATURE                   Location/Qualifiers
misc_feature              1..48
                          note = substrate strand of enzymes
modified_base             6
                          mod_base = OTHER
                          note = 6-carboxyfluorescein modification
modified_base             23
                          mod_base = OTHER
                          note = internal abasic site tetrahydrofuran modification
source                    1..48
                          mol_type = other DNA
                          organism = synthetic construct
SEQUENCE: 1
ctggatacac gaactttaag canagtcaat gaaggacgca tatcagtg              48

SEQ ID NO: 2              moltype = DNA  length = 48
FEATURE                   Location/Qualifiers
misc_feature              1..48
                          note = substrate strand of enzymes
modified_base             42
                          mod_base = OTHER
                          note =
                          2-[N-(2-hydroxyethyl)-4-[[2-methoxy-5-methyl-4-[(4-methyl-2
                          -nitrophenyl)diazenyl]phenyl]diazenyl]anilino]ethanol
                          modification
source                    1..48
                          mol_type = other DNA
                          organism = synthetic construct
SEQUENCE: 2
cactgatatg cgtccttcat tgactctgct taaagttcgt gtatccag              48
```

TREATMENTS OF PROSTATE CANCER

CROSS-REFERENCE TO RELATED APPLICATION

This application is a Continuation Application of U.S. patent application Ser. No. 17/697,306, filed Mar. 17, 2022, now U.S. Pat. No. 11,478,496; which is a Continuation Application of U.S. patent application Ser. No. 16/751,696, filed Jan. 24, 2020, now U.S. Pat. No. 11,304,969, all of which are hereby incorporated by reference in their entireties, including all figures, tables, and drawings.

SEQUENCE LISTING

The Sequence Listing for this application is labeled "SeqList-03Apr23.xml" which was created on Apr. 3, 2023 and is 5,526 bytes. The Sequence Listing is incorporated herein by reference in its entirety.

BACKGROUND

Prostate cancer is the second most frequently diagnosed cancer among men. The disease is a major cause of seriously impaired quality of life and is a leading cause of cancer mortality for the elderly male population. When detected early, the localized disease can be effectively treated with a prostatectomy. Advanced cancer that has metastasized beyond the prostate is often treated with castration therapies. Treatment of advanced cancer often involves surgery, radiation therapy, external beam radiation therapy, high intensity focused ultrasound, chemotherapy including oral chemotherapeutic agents, cryosurgery, hormonal therapy, or a combination thereof. Although androgen deprivation therapy (ADT) through either chemical or surgical castration works initially to control metastatic prostate cancer, the cancer often progresses to treatment resistant prostate cancer, such as castration resistant prostate cancer (CRPC) or hormone refractory prostate cancer (HRPC). There is no efficient therapy available for the treatment of resistant prostate cancer, with 75% of patients dying within five years of disease onset.

High throughput genetic screening technologies, such as transcriptomics and next generation sequencing, have led to the stratification of prostate cancer into well-defined molecular subclasses, making it clear that changes to the DNA damage and repair pathways are an intrinsic part of prostate cancer progression to CRPC.

An erythroblast transformation-specific (ETS) gene fusion, which is found in nearly 80% of advanced cancers, induces DNA damage and correlates with increased patient mortality. DNA repair pathways, which can minimize potentially mutagenic consequences of DNA damage, are altered in 27% of metastatic prostate cancers. DNA repair pathways are broadly characterized into three forms: base excision repair (BER), mismatch repair (MMR), and nucleotide excision repair (NER). The increased expression of DNA repair-associated genes in general and BER-associated genes, in particular, correlates with rapid recurrence, metastatic dissemination, and decreased patient survival. These findings suggest that the DNA repair machinery may be a therapeutic target in most advanced prostate cancers. Deficiencies in DNA damage repair underlie the pathogenesis of cancer as well as many genetic disorders, such as Xeroderma pigmentosum, Cockayne syndrome, and Ataxia-telangiectasia.

BER is an essential DNA repair pathway in mammalian cells, which removes a variety of DNA base lesions generated endogenously and exogenously by DNA damaging agents. It also repairs single-strand DNA (ssDNA) breaks through the coordination among DNA polymerase β (pol β), poly (ADP-ribose) polymerase 1 (PARP1), X-ray cross-complementing protein 1 (XRCC1), and other BER cofactors. There are two BER sub-pathways: single-nucleotide (SN) and long-patch (LP) BER. SN-BER is initiated by the removal of a damaged DNA base by a damage-specific DNA glycosylase. This leaves an abasic site that is 5'-incised by AP endonuclease 1 (APE1) resulting in a one nucleotide-gapped intermediate with a 5'-deoxyribose phosphate (dRP) group. Subsequently, a native dRP group is directly removed by the dRP lyase activity of pol β. Pol β then fills in the gap with its polymerase activity leaving a nicked DNA, which is sealed by DNA ligases, e.g. DNA Ligase I (LIG I) and LIG IIIα. In this scenario, only one nucleotide is replaced.

In LP-BER, a modified dRP group, such as an oxidized dRP, which is refractory to the dRP lyase activity of pol β, is removed by flap endonuclease 1 (FEN1). This leaves a one-nucleotide gap that is then filled in by pol β creating a nick sealed by LIG I. Alternatively, pol β can continuously perform the strand-displacement DNA synthesis to create a 5'-flap with a dRP group. FEN1 removes the flap, and LIG I seals the nick to accomplish the long-patch BER. In this scenario, a longer nucleotide segment with 2-10 nucleotides is replaced.

To facilitate the efficient BER, several co-factors, such as PARP1 and proliferating cell nuclear antigen (PCNA), coordinate and stimulate the activities of the core enzymes, pol β and FEN1. PARP1 is activated in response to ssDNA breaks and catalyzes poly (ADP) ribosylation of XRCC1. XRCC1-DNA ligase III (LIG III) complex is recruited to the strand breaks and facilitates the ligation of the nicked DNA. PARP1 can also coordinate with APE1 and FEN1 to modulate the efficiency of pol β-mediated LP-BER.

To date, no attempts that target core enzymes of BER in prostate cancer have been made. Rapid development of resistance to PARP inhibitors makes it critically important to identify orthogonal suppressors of BER capacity. There is also a need to develop compositions and methods for treating prostate cancer, in particular, advanced prostate cancer, by reducing BER capacity through, for example, the inhibition of key BER enzymes, such as pol β and LIG I.

BRIEF DESCRIPTION OF THE INVENTION

The present invention provides compounds, compositions and methods for treating prostate cancers, preferably, advanced prostate cancers. The subject invention also provides compounds, compositions and methods for preventing/slowing down/reducing the progress and proliferation of prostate cancer cells. The subject invention further provides compounds, compositions and methods for reducing the recurrence of prostate cancer.

Compounds, compositions and methods of the subject invention can inhibit DNA repair within cancer/tumor cells to slow tumor growth. Advantageously, such compounds, compositions and methods according to the subjection invention can effectively block DNA repair in cancer cells without affecting normal cell growth.

The subject invention also provides compounds, compositions and methods for inhibiting/reducing BER capacity in cancers, preferably, prostate cancers. The subject invention further provides compounds, compositions and methods for inhibiting/reducing BER enzymes such as pol β and LIG I in prostate cancer cells.

The subject invention repurposes drugs that have already been approved by FDA for human use, providing a high benefit to risk pathway for drugs with a newly identified clinical application to impact patient treatment in the clinic. New therapeutic treatment options that are herein identified for, e.g., CRPC, will therefore improve the disease outcome and quality of life for the men affected.

The compounds that have been herein identified, according to the subject invention, to have one or more activities of inhibiting/reducing BER capacity, inhibiting/reducing enzymes, pol β and LIG I, required by BER, preventing/slowing down/reducing the progress and proliferation of prostate cancer cells, and treating prostate cancers include natamycin, calcipotriene, ceftazidime, nystatin, prasugrel, sirolimus (Rapamycin), flecainide acetate, dihydroergotamine mesylate, risperidone, dipyridamole, doxycycline monohydrate, methylergonovine maleate, paliperidone, reserpine, and sunitinib malate.

In one embodiment, the subject invention provides compositions comprising one or more compounds according to the subject invention and a pharmaceutically acceptable carrier, wherein the one or more compounds are selected from natamycin, calcipotriene, ceftazidime, nystatin, prasugrel, sirolimus, flecainide acetate, dihydroergotamine mesylate, risperidone, dipyridamole, doxycycline monohydrate, methylergonovine maleate, paliperidone, reserpine, and sunitinib malate.

In one embodiment, the composition comprises one or more, two or more, three or more, or four or more compounds selected from natamycin, calcipotriene, ceftazidime, nystatin, and prasugrel.

BRIEF DESCRIPTION OF THE DRAWINGS

FIGS. 7A-7E show that androgen-dependent prostate cancer cell lines are more sensitive to natamycin treatment. (7A) LNCaP cells were plated in 10% FBS supplemented medium at $10^4$ cells per well onto E-plates and treated with vehicle, 0.1 µM, 1 µM, or 10 µM of natamycin. (7B) LNCaP cells were plated in medium supplemented with 10% CSS at $10^4$ cells/well and treated as in 7A. (7C) PNT1A cells were plated in medium supplemented with 10% CSS at $5 \times 10^4$ cells per well and treated as in 7A. (7D) LNCaP cells were plated in medium supplemented with 10% CSS or 10% FBS and cells were allowed to attach. Next day, cells were treated with vehicle, 0.1 µM, 1 µM, 2.5 µM, 5 µM, or 10 µM of natamycin. Forty eight hours later cellular viability was compared using MTT assay. (7E) LNCaP cells were grown in complete medium and treated for 48 h with 10 µM of indicated compounds. Protein was extracted and AR, γ-H2AX, and tubulin levels compared by Western blotting. Impedance in 7A-7C was measured every 30 min and values were normalized to those at the time of treatment. (*signifies a difference between vehicle and treatment with p≤0.01, **p≤0.0001)

BRIEF DESCRIPTION OF SEQUENCES

Figure 1:
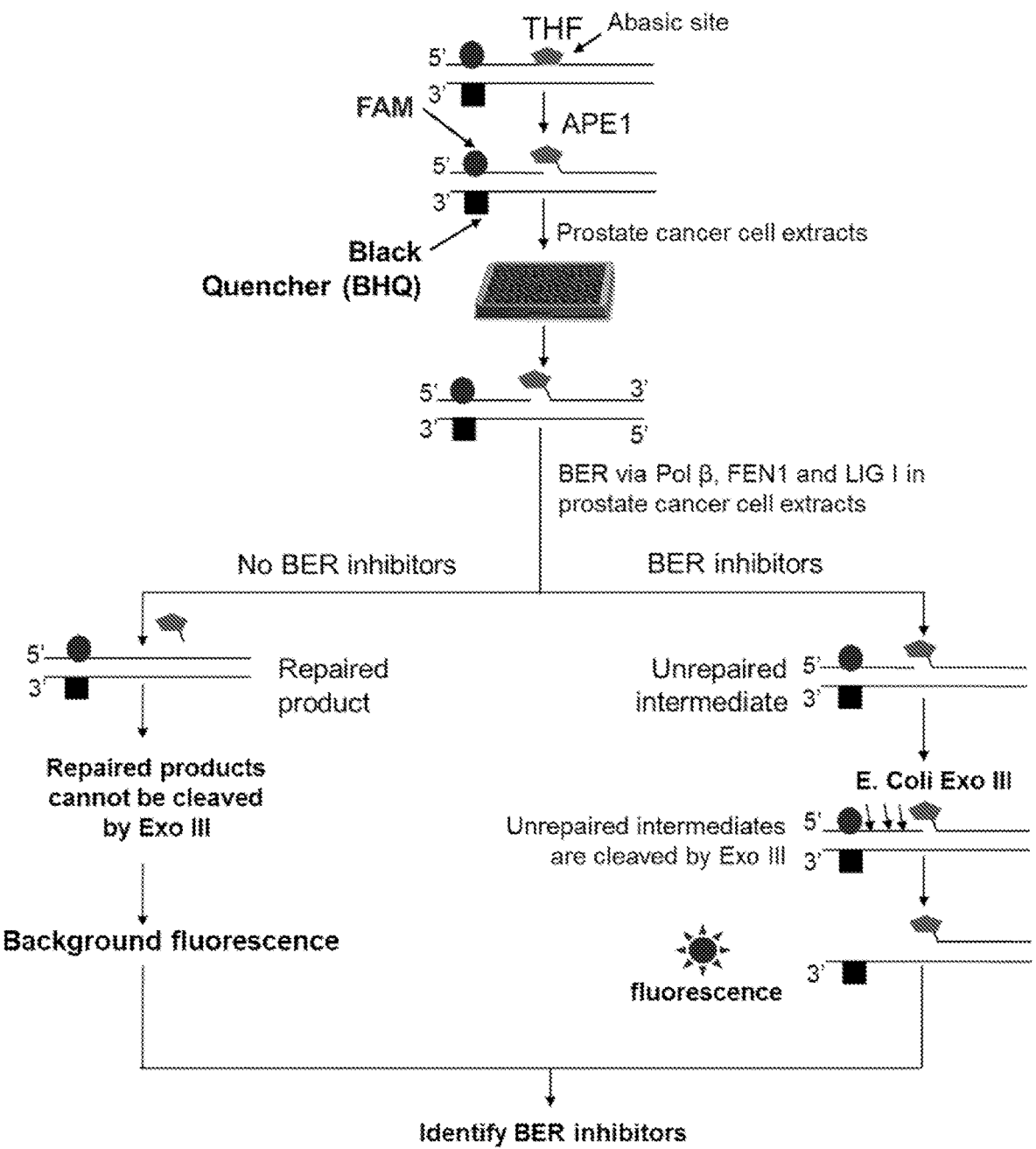
FIG. 1 shows a schematic diagram of the fluorescence-based high throughput screening of BER capacity inhibitors. A fluorescence-tagged oligonucleotide substrate that contains the analog of an abasic lesion, tetrahydrofuran (THF) was employed to determine the inhibitory effects of 774 compounds from The Screen-Well® FDA Approved Drug Library V2 on the BER capacity of prostate cancer whole cell extracts. The procedure of the screening was conducted as described below in the "Materials and Methods" section.

SEQ ID NO: 1 is an oligonucleotide for constructing the upper strand of substrate contemplated for use according to the subject invention.

SEQ ID NO: 2 is an oligonucleotide for constructing the bottom strand of substrate contemplated for use according to the subject invention.

DETAILED DESCRIPTION OF THE INVENTION

The present invention provides compounds, compositions and methods for treating prostate cancers, preferably, advanced prostate cancers. The subject invention also provides compounds, compositions and methods for preventing/slowing down/reducing the progress and proliferation of prostate cancer cells. The subject invention further provides compounds, compositions and methods for reducing the recurrence of prostate cancer.

The subject invention provides compounds, compositions and methods for inhibiting DNA repair within cancer cells to slow tumor growth. Advantageously, such compounds, compositions and methods according to the subjection invention can effectively block DNA repair in cancer cells without affecting normal cell growth.

The subject invention also provides compounds, compositions and methods for inhibiting/reducing BER capacity in cancer cells. The subject invention further provides compounds, compositions and methods for inhibiting/reducing BER enzymes such as pol β and LIG I.

In other embodiments, the compounds of the subject invention can also be used in treating other cancers and relieving the symptoms of neurodegenerative disorders including, for example, Alzheimer's, Huntington's and Parkinson's diseases. Other cancers include, but are not limited to, fibrosarcoma, myxosarcoma, liposarcoma, chondrosarcoma, osteogenic sarcoma, chordoma, lymphangioendotheliosarcoma, angiosarcoma, endotheliosarcoma, lymphangiosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, neuroblastoma, and retinoblastoma.

Compositions

In specific embodiments, the subject invention provides compounds and compositions comprising such compounds for treating prostate cancer, inhibiting/slowing down the progress and proliferation of prostate cancer cells, inhibiting DNA repair within prostate cancer cells, and reducing BER capacity. In a preferred embodiment, the prostate cancer is CRPC.

The compounds that can be used according to the subject invention include natamycin, calcipotriene, ceftazidime, nystatin, prasugrel, sirolimus (Rapamycin), flecainide acetate, dihydroergotamine mesylate, risperidone, dipyridamole, doxycycline monohydrate, methylergonovine maleate, paliperidone, reserpine, and sunitinib malate. In a preferred embodiment, the compounds that can be used according to the subject invention include natamycin, calcipotriene, ceftazidime, nystatin, and prasugrel.

In one embodiment, the subject invention provides compositions comprising one or more compounds according to the subject invention and a pharmaceutically acceptable carrier, wherein the one or more compounds are selected from natamycin, calcipotriene, ceftazidime, nystatin, prasugrel, sirolimus (Rapamycin), flecainide acetate, dihydroergotamine mesylate, risperidone, dipyridamole, doxycycline monohydrate, methylergonovine maleate, paliperidone, reserpine, and sunitinib malate.

In a further embodiment, the composition comprises two or more, three or more, four or more, or five or more compounds selected from natamycin, calcipotriene, ceftazidime, nystatin, prasugrel, sirolimus (Rapamycin), flecainide acetate, dihydroergotamine mesylate, risperidone, dipyridamole, doxycycline monohydrate, methylergonovine maleate, paliperidone, reserpine, and sunitinib malate.

In one embodiment, the composition comprises one or more, two or more, three or more, or four or more compounds selected from natamycin, calcipotriene, ceftazidime, nystatin, and prasugrel. These five compounds are functionally disparate molecules with antifungal and anti-bacterial properties, a vitamin D agonist, and an ADP receptor inhibitor.

In a specific embodiment, the composition comprises natamycin, a polyene macrolide antibiotic with broad antifungal activity and low toxicity against mammalian cells.

In a further embodiment, the composition comprises at least natamycin. The composition may comprise, for example, any of the following:
1) natamycin and calcipotriene;
2) natamycin and ceftazidime;
3) natamycin and nystatin;
4) natamycin and prasugrel;
5) natamycin, calcipotriene and ceftazidime;
6) natamycin, calcipotriene and nystatin;
7) natamycin, calcipotriene and prasugrel;
8) natamycin, ceftazidime and nystatin;
9) natamycin, ceftazidime and prasugrel;
10) natamycin, nystatin and prasugrel;
11) natamycin, calcipotriene, ceftazidime and nystatin;
12) natamycin, calcipotriene, ceftazidime and prasugrel; or
13) natamycin, calcipotriene, ceftazidime, nystatin and prasugrel.

In one embodiment, the compounds may be in a pharmaceutically acceptable salt form or a form of free base. Examples of pharmaceutically acceptable salts include, without limitation, the nontoxic inorganic and organic acid addition salts such as acetate, aconate, ascorbate, benzenesulfonate, benzoate, cinnamate, citrate, embonate, enantate, formate, fumarate, glutamate, glycolate, hydrochloride, hydrobromide, lactate, maleate, alonate, mandelate, methanesulfonate, naphthalene-2-sulphonate, nitrate, perchlorate, phosphate, phthalate, salicylate, sorbate, stearate, succinate, sulphate, tartrate, toluene-p-sulphonate, and the like.

Suitable acids for use in the preparation of pharmaceutically acceptable salts of a compound described herein, include, but are not limited to, aceptic acid; 2,2-dichloroacetic acid; acylated amino acids; adipic acid; alginic acid; ascorbic acid; L-aspartic acid; benzenesulfonic acid; benzoic acid; 4-acetamidobenzoic acid; boric acid; (+)-camphoric acid; camphorsulfonic acid; (+)-(1S)-camphor-10-sulfonic acid; capric acid; caproic acid; caprylic acid; cinnamic acid; citric acid; cyclamic acid; cyclohexanesulfamic acid; dodecylsulfuric acid; ethane-1,2-disulfonic acid; ethanesulfonic acid; 2-hydroxyethanesulfonic acid; formic acid; fumaric acid; galactaric acid; gentisic acid; glucoheptonic acid; D-gluconic acid; D-glucuronic acid; L-glutamic acid; α-oxo-glutaric acid; glycolic acid; hippuric acid; hydrobromic acid; hydrochloric acid; hydroiodic acid; (+)-L-lactic acid; (+/−)-DL-lactic acid; lactobionic acid; lauric acid; maleic acid; (−)-L-malic acid; malonic acid; (+/−)-DL-mandelic acid; methanesulfonic acid; naphthalene-2-sulfonic acid; naphthalene-1,5-disulfonic acid; 1-hydroxy-2-napthoic acid; nicotinic acid; nitric acid; oleic acid; orotic acid; oxalic acid; palmitic acid; pamoic acid; perchloric acid; phosphoric acid; L-pyroglutamic acid; saccharic acid; salicyclic acid; 4-amino-salicylic acid; sebacic acid; stearic acid; succinic acid; sulfuric acid; tannic acid; (+)-L-tartaric acid; thiocyanic acid; p-toluenesulfonic acid; undecylenic acid; and valeric acid.

In one embodiment, the composition according to the subject invention also comprises a pharmaceutically acceptable carrier. "Pharmaceutically acceptable carrier" refers to a diluent, adjuvant or excipient with which the one or more active agents disclosed herein can be formulated. Typically, a "pharmaceutically acceptable carrier" is a substance that is non-toxic, biologically tolerable, and otherwise biologically suitable for administration to a subject, such as an inert substance, added to a pharmacological composition or otherwise used as a diluent, adjuvant or excipient to facilitate administration of the composition disclosed herein and that is compatible therewith.

Examples of carriers suitable for use in the pharmaceutical compositions are known in the art and such embodiments are within the purview of the invention. The pharmaceutically acceptable carriers and excipients, including, but not limited to, aqueous vehicles, water-miscible vehicles, non-aqueous vehicles, stabilizers, solubility enhancers, isotonic agents, buffering agents, suspending and dispersing agents, wetting or emulsifying agents, complexing agents, sequestering or chelating agents, cryoprotectants, lyoprotectants, thickening agents, pH adjusting agents, and inert gases. Other suitable excipients or carriers include, but are not limited to, dextran, glucose, maltose, sorbitol, xylitol, fructose, sucrose, and trehalose.

In one embodiment, the composition further comprises an antiandrogen agent including, but not limited to, cyproterone acetate, flutamide, nilutamide, bicalutamide, enzalutamide, Eulexin®, Casodex®, Nilandron® and Nizoral®.

In one embodiment, the composition further comprises an inhibitor of the PARP1, an enzyme required for efficient BER. The PARP1 inhibitors include, but are not imitated to, CCDC6, rucaparib (NCT02952534, NCT03533946 and NCT03413995) and olaparib (NCT02316197, NCT03012321, NCT03787680, NCT03432897 etc.).

In some embodiments, the composition may comprise a chemotherapeutic agent, including, but not limited to, thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triety lenephosphoramide, triethiy lenethiophosphoramide and tiimethy lolomelamine; acetogenins (e.g., bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB 1-TM1); eleutherobin; pancratistatin; sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; vinca alkaloids; epipodophyllotoxins; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitiaerine; pentostatin; phenamet; pirarubicin; losoxantione; podophyllinic acid; 2-ethylhydrazide; procarbazine; razoxane; rhizoxin; sizofiran; spirogermanium; tenuazonic acid; urethan; vindesine; dacarbazine; mannomustine; mitobronitol; mitolactol; pipobroman;

gacytosine; cyclophosphamide; thiotepa; chloranbucil; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; novantrone; teniposide; edatrexate; daunomycin; aminopterin; xeloda; ibandronate; irinotecan (e.g., CPT-11); difluoromethylornithine (DFMO); retinoids such as retinoic acid; capecitabine; leucovorin (LV); irenotecan; adrenocortical suppressant; adrenocorticosteroids; progestins; and pharmaceutically acceptable salts, acids or derivatives of any of the above.

In certain embodiments, the composition disclosed herein may also comprise an anti-fungal agent, including, but not limited to, amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, oxyconazole, ravuconazole, posaconazole, rimocidin, sertaconazole, sulconazole, terbinafine, terconazole, tioconazole, and voriconazole.

In certain embodiments, the composition may comprise an antibiotic, including, but not limited to, amoxicillin, ampicillin, arsphenamine, azithromycin, aztreonam, azlocillin, bacitracin, carbenicillin, cefaclor, cefadroxil, cefamandole, cefazolin, cephalexin, cefdinir, cefditoren, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clindamycin, clofazimine, cloxacillin, colistin, dalfopristan, demeclocycline, dicloxacillin, dirithromycin, doxycycline, erythromycin, enafloxacin, enviomycin, ertepenem, ethambutol, flucloxacillin, fosfomycin, furazolidone, gatifloxacin, geldanamycin, gentamicin, herbimicin, imipenem, linezolid, lomefloxacin, loracarbef, mafenide, moxifloxacin, meropenem, metronidazole, mezlocillin, minocycline, mupirozin, nafcillin, neomycin, netilmicin, nitrofurantoin, norfloxacin, oxy tetracycline, penicillin, piperacillin, platensimycin, polymixin B, prochlorperazine, prontocil, quinupristine, rifabutin, roxithromycin, spectinomycin, sulfacetamide, sulfamethizole, sulfamethoxazole, teicoplanin, telithromycin, tetracycline, thioacetazone, thioridazine, ticarcillin, tobramycin, trimethoprim, troleandomycin, trovafloxacin, and vancomycin.

In one embodiment, the composition may comprise a steroidal drug known in the art, including, but not limited to, aldosterone, beclometasone, betamethasone, deoxycorticosterone acetate, fludrocortisone acetate, hydrocortisone, prednisolone, prednisone, methylprenisolone, dexamethasone, and triamcinolone.

The pharmaceutical composition is used for convenient and effective administration in effective amounts with a suitable pharmaceutically acceptable carrier in an acceptable dosage unit. In the case of compositions containing supplementary active ingredients, the dosages may be determined by reference to the usual dose and manner of administration of the said ingredients.

In one embodiment, the pharmaceutical composition comprising compounds according to the invention, together with a conventional adjuvant, carrier, or diluent, may thus be placed into the form of solids including tablets, filled capsules, powder and pellet forms, and liquids such as aqueous or non-aqueous solutions, suspensions, emulsions, elixirs, and capsules filled with the same. The composition may further comprise conventional ingredients in conventional proportions, with or without additional active compounds.

In a further embodiment, the composition is in the powder form. The pharmaceutically accepted carrier is a finely divided solid, which is in a mixture with the finely divided active compounds. In another embodiment, the composition is in the tablet form. The active component is mixed with the pharmaceutically accepted carrier having the necessary binding capacity in suitable proportions and compacted in desired shape and size. Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

In a further embodiment, the composition is in other solid forms including capsules, pills, cachets, and lozenges, which are suitable for oral administration.

In one embodiment, the composition is formulated in accordance with routine procedures as a pharmaceutical composition adapted for local administration to humans. Typically, compositions for local administration are solutions in a sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is administered by injection, an ampoule of sterile water for injection or saline can be provided so that the ingredients may be mixed prior to administration.

The pharmaceutical composition of the subject invention may be administered rectally or urethrally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas.

Rectal and urethral suppositories are solid bodies for insertion into body orifices, which are solid at ordinary temperatures but melt or soften at body temperature to release the active ingredient(s) inside the orifices. Pharmaceutically acceptable carriers utilized in rectal and urethral suppositories include bases or vehicles, such as stiffening agents, which produce a melting point in the proximity of body temperature. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di and triglycerides of fatty acids, hydrogels, such as polyvinyl alcohol, hydroxyethyl methacrylate, poly acrylic acid; glycerinated gelatin. Combinations of the various vehicles may be used. The typical weight of a rectal and vaginal suppository is about 2 to about 3 g.

The pharmaceutical compositions may be formulated in any forms that are suitable for parenteral administration, including solutions, suspensions, emulsions, micelles, liposomes, microspheres, nanosystems, semi-solid, and solid forms suitable for solutions or suspensions in liquid prior to injection.

The composition may be formulated in a controlled release formulation, including implants and microencapsulated delivery systems. In one embodiment, the pharmaceutical composition can be dispersed in a solid inner matrix surrounded by an outer polymeric membrane that is insoluble in body fluids but allows the active ingredient in the pharmaceutical compositions to diffuse through. Suitable inner matrixes include polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers, such as hydrogels of esters of acrylic and methacrylic acid, collagen, cross-linked polyvinylalcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

The pharmaceutical compositions of the subject invention may be formulated to be immediate release or modified release, including delayed-, sustained-, pulsed-, controlled-, targeted, and programmed release. The pharmaceutical compositions in modified release dosage forms can be prepared using a variety of modified release devices and methods known to those skilled in the art, including, but not limited to, matrix-controlled release devices, osmotic controlled release devices, multiparticulate controlled release devices, ion-exchange resins, enteric coatings, multilayered coatings, microspheres, liposomes, and combinations thereof. For example, the pharmaceutical composition may also be formulated into liposomes to reduce toxicity or increase bioavailability.

Methods

The present invention provides methods for treating cancer, preferably, prostate cancer comprising administering to a subject in need of such treatment an effective amount of pharmaceutical composition of the subject invention.

In one embodiment, the prostate cancer treated according to the subject invention may be, e.g., organ-confined primary prostate cancer, locally invasive advanced prostate cancer, metastatic prostate cancer, castration-resistant prostate cancer (CRPC) or recurrent CRPC. Metastatic prostate cancer is characterized by prostate cancer cells that are no longer organ-confined.

In one embodiment, the subject has been diagnosed with prostate cancer, preferably, CRPC. Those skilled in the art would know how to identify a subject with prostate cancer. For example, a prostate specific antigen (PSA) test, imaging techniques (for example X-rays, MRIs, CT scans and bone scans), lymph node examinations, biopsies, and digital rectal examinations can be performed to identify or diagnose a subject with prostate cancer.

The term "subject" or "patient," as used herein, describes an organism, including mammals such as primates. Mammalian species that can benefit from the disclosed methods of treatment include, but are not limited to, apes, chimpanzees, orangutans, humans, and monkeys; domesticated animals such as dogs, cats; live stocks such as horses, cattle, pigs, sheep, goats, and chickens; and other animals such as mice, rats, guinea pigs, and hamsters. The subject may be diagnosed with prostate cancer of grade II or higher.

In a preferred embodiment, the subject is a male human.

In one embodiment, the method for treating prostate cancer comprises administering to a subject in need of such treatment an effective amount of a pharmaceutical composition comprising one or more compounds selected from natamycin, calcipotriene, ceftazidime, nystatin, prasugrel, sirolimus (Rapamycin), flecainide acetate, dihydroergotamine mesylate, risperidone, dipyridamole, doxycycline monohydrate, methylergonovine maleate, paliperidone, reserpine, and sunitinib malate.

In one embodiment, the method for treating prostate cancer comprises administering to a subject in need of such treatment an effective amount of a pharmaceutical composition comprising natamycin. In a further embodiment, the composition further comprises one or more compounds selected from calcipotriene, ceftazidime, nystatin, prasugrel, sirolimus (Rapamycin), flecainide acetate, dihydroergotamine mesylate, risperidone, dipyridamole, doxycycline monohydrate, methylergonovine maleate, paliperidone, reserpine, and sunitinib malate.

The terms "treatment" or any grammatical variation thereof (e.g., treat, treating, etc.), as used herein, includes but is not limited to, the application or administration to a subject (or application or administration to a cell or tissue from a subject) with the purpose of delaying, slowing, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indication of success in the treatment or amelioration of a pathology or condition, including any objective or subjective parameter such as abatement; remission; lessening of the rate of worsening; lessening severity of the disease; stabilization, diminishing of symptoms or making the pathology or condition more tolerable to the subject; or improving a subject's physical or mental well-being. Treating can also include preventing a condition or disorder, which, as used herein, means delaying the onset of, or progression of, a particular sign or symptom of the condition or disorder.

In one embodiment, the subject invention provides methods for preventing/slowing down/reducing/inhibiting the progress and proliferation of prostate cancer cells comprising administering to a subject in need of such prevention/slowing down/reduction an effective amount of a pharmaceutical composition of the subject invention.

In one embodiment, the method for preventing/slowing down/reducing the progress and proliferation of prostate cancer cells comprises administering to a subject in need an effective amount of a pharmaceutical composition comprising one or more compounds selected from natamycin, calcipotriene, ceftazidime, nystatin, prasugrel, sirolimus (Rapamycin), flecainide acetate, dihydroergotamine mesylate, risperidone, dipyridamole, doxycycline monohydrate, methylergonovine maleate, paliperidone, reserpine, and sunitinib malate.

In one embodiment, the method for preventing/slowing down/reducing the progress and proliferation of prostate cancer cells comprises administering to a subject in need an effective amount of a pharmaceutical composition comprising natamycin. In a further embodiment, the composition further comprises one or more compounds selected from calcipotriene, ceftazidime, nystatin, prasugrel, sirolimus (Rapamycin), flecainide acetate, dihydroergotamine mesylate, risperidone, dipyridamole, doxycycline monohydrate, methylergonovine maleate, paliperidone, reserpine, and sunitinib malate.

The term "prevention" or any grammatical variation thereof (e.g., prevent, preventing, etc.), as used herein, includes but is not limited to, at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). The term "prevention" may refer to avoiding, delaying, forestalling, or minimizing one or more unwanted features associated with a disease or disorder, and/or completely or almost completely preventing the development of a disease or disorder and its symptoms altogether. Prevention can further include, but does not require, absolute or complete prevention, meaning the disease or disorder may still develop at a later time and/or with a lesser severity than it would without preventative measures. Prevention can include reducing the severity of the onset of a disease or disorder, and/or inhibiting the progression thereof.

In one embodiment, the prostate cancer cells are androgen dependent and require BER for optimal viability and proliferation.

In one embodiment, the subject invention provides methods for reducing the recurrence of prostate cancer comprising administering to a subject in need of such reduction an effective amount of a pharmaceutical composition of the subject invention. In specific embodiments, the subject has had prostate cancer and prostate cancer treatments and/or has a risk for the reappearance of prostate cancer. Preferably, the prostate cancer is an advanced prostate cancer such as CRPC.

The subject may have had prostate cancer treatments, including, but not limited to, orchiectomy (surgical castration), prostatectomy, anti-androgen therapy (for example, Eulexin®, Casodex®, Nilandron® and Nizoral®) radiation therapy, chemotherapy, luteinizing hormone releasing hormone analogs (for example, Lupron®, Viadur®, Eligard®, Zoladex®, Trelstar® and Vantas®), lutenizing hormone releasing hormone antagonists (for example, Plenaxis® and) Firmagon® or combinations of these treatment methods.

As used herein, reducing the recurrence of prostate cancer refers to preventing, precluding, delaying, averting, obviating, forestalling, stopping, or hindering the onset, incidence or severity of the reappearance of prostate cancer in a subject. The reappearance of prostate cancer means the reappearance of one or more clinical symptoms of prostate cancer after a period devoid of these clinical symptoms. The recurrence of prostate cancer can be after treatment for prostate cancer or after a remission. A recurrence may occur days, weeks, months or years after treatment or after a remission. One or more symptoms of prostate cancer may be, e.g., problems urinating, pain during urination, pelvic discomfort, swelling in the legs as a result of edema, blood in urine, swelling of the lymph glands, and/or bone pain in a subject. The reduction or delay in onset, incidence or severity of recurrence of prostate cancer can be about a 5, 10, 20, 30, 40, 50, 60, 70, 80, 90, 100%, or any amount of reduction in between.

In one embodiment, the method for reducing the recurrence of prostate cancer comprises administering to a subject in need a pharmaceutically effective amount of composition comprising one or more compounds selected from natamycin, calcipotriene, ceftazidime, nystatin, prasugrel, sirolimus (Rapamycin), flecainide acetate, dihydroergotamine mesylate, risperidone, dipyridamole, doxycycline monohydrate, methylergonovine maleate, paliperidone, reserpine, and sunitinib malate.

In one embodiment, the method for reducing the recurrence of prostate cancer comprises administering to a subject in need a pharmaceutically effective amount of composition comprising natamycin. In a further embodiment, the composition further comprises one or more compounds selected from calcipotriene, ceftazidime, nystatin, prasugrel, sirolimus (Rapamycin), flecainide acetate, dihydroergotamine mesylate, risperidone, dipyridamole, doxycycline monohydrate, methylergonovine maleate, paliperidone, reserpine, and sunitinib malate.

In one embodiment, the subject invention provides methods for inhibiting DNA repair within prostate cancer cells comprising contacting prostate cancer cells with an amount of a pharmaceutical composition of the subject invention effective to inhibit DNA repair within prostate cancer cells.

In one embodiment, the method for inhibiting DNA repair within prostate cancer cells comprises contacting prostate cancer cells with an effective amount of a pharmaceutical composition comprising one or more compounds selected from natamycin, calcipotriene, ceftazidime, nystatin, prasugrel, sirolimus (Rapamycin), flecainide acetate, dihydroergotamine mesylate, risperidone, dipyridamole, doxycycline monohydrate, methylergonovine maleate, paliperidone, reserpine, and sunitinib malate.

In a specific embodiment, the method for inhibiting DNA repair within prostate cancer cells comprises contacting prostate cancer cells with an effective amount of a pharmaceutical composition comprising natamycin. In a further embodiment, the method for inhibiting DNA repair within prostate cancer cells may further comprises contacting prostate cancer cells with an effective amount of one or more compounds selected from calcipotriene, ceftazidime, nystatin, prasugrel, sirolimus (Rapamycin), flecainide acetate, dihydroergotamine mesylate, risperidone, dipyridamole, doxycycline monohydrate, methylergonovine maleate, paliperidone, reserpine, and sunitinib malate.

In one embodiment, the subject invention provides methods for inhibiting/slowing prostate tumor growth in a subject comprising administering to the subject with a prostate tumor an effective amount of a pharmaceutical composition of the subject invention. Alternatively and additionally, the method for inhibiting/slowing prostate tumor growth comprises contacting the prostate tumor with an amount of composition of the subject invention effective to inhibit prostate tumor growth.

In one embodiment, the method for inhibiting/slowing prostate tumor growth in a subject comprises administering to a subject in need an effective amount of a pharmaceutical composition comprising one or more compounds selected from natamycin, calcipotriene, ceftazidime, nystatin, prasugrel, sirolimus (Rapamycin), flecainide acetate, dihydroergotamine mesylate, risperidone, dipyridamole, doxycycline monohydrate, methylergonovine maleate, paliperidone, reserpine, and sunitinib malate.

In one embodiment, the method for inhibiting/slowing prostate tumor growth in a subject comprises administering to a subject in need an effective amount of a pharmaceutical composition comprising natamycin. In a further embodiment, the composition comprises one or more compounds selected from calcipotriene, ceftazidime, nystatin, prasugrel, sirolimus (Rapamycin), flecainide acetate, dihydroergotamine mesylate, risperidone, dipyridamole, doxycycline monohydrate, methylergonovine maleate, paliperidone, reserpine, and sunitinib malate.

In one embodiment, the subject invention provides methods for inhibiting/reducing BER capacity in prostate cancer cells by inhibiting/reducing BER enzymes such as pol β and LIG I. The method comprises administering to a subject in need of an effective amount of a pharmaceutical composition of the subject invention. The method further comprises contacting the prostate cancer cells with a pharmaceutical composition of the subject invention effective to reduce BER capacity in the prostate cancer cells.

The methods set forth herein can be utilized in a subject that has been treated with an antiandrogen or antiandrogen receptor agent or has been treated with an androgen deprivation therapy (ADT). ADT refers to a type of treatment for prostate cancer that suppresses male hormones, androgens. Prostate cells are dependent on androgens, and therefore, suppression of androgens can reduce or inhibit the growth of prostate cells, such as prostate cancer cells. Examples of ADT include surgical methods and drug-based methods. Surgical ADT involves orchiectomy, which is also known as castration. Surgical ADT can cause the subject's body to no longer produce testosterone, which is needed for the growth of prostate cancer cells. Drug-based ADT can include administration of an LHRH agonist or an LHRH antagonist (e.g., degarelix), a CYP17 inhibitor, and/or an antiandrogen. Antiandrogen refers to a molecule that can block the body's ability to use or respond to androgens. Examples of antiandrogens include cyproterone acetate, flutamide, nilutamide, bicalutamide, enzalutamide, Eulexin®, Casodex®, Nilandron® and Nizoral®.

Any of the methods set forth herein, can further comprise administering an anti-inflammatory agent to the subject. Examples of anti-inflammatory agents include, but are not limited to anti-monocyte chemotactic protein 1 (anti-CCL2) monoclonal antibody, anti-CCL3 monoclonal antibody and anti-CCL4 monoclonal antibody, ImSAIDs, NSAIDS and steroids.

The compositions of the present invention can be administered to the subject being treated by standard routes, including the local, oral, ophthalmic, nasal, topical, transdermal, intra-articular, parenteral (e.g., intravenous, intraarterial, intraperitoneal, intrathecal, intraventricular, intradermal, intracavity, subcutaneous or intramuscular), intracranial, intracerebral, intraspinal, intrauterine, or rectal route. Depending on the condition being treated, one route may be preferred over others, which can be determined by those skilled in the art. Preferably, the composition is administered by injection (e.g., IV injection), gradual infusion over time or implantation.

Depending on the route of administration, the pharmaceutical composition can be coated with a material to protect the pharmaceutical composition from the action of enzymes, acids, and other natural conditions that may inactivate the pharmaceutical composition. Dispersions can also be prepared in glycerol, liquid polyethylene glycols, and mixtures thereof, and in oils. Under ordinary conditions of storage and use, these preparations may contain a preservative to prevent the growth of microorganisms.

Administration can be carried out using therapeutically effective amounts of the agents described herein for periods of time effective according to the subject invention. The effective amount may be determined by one of ordinary skill in the art and includes exemplary dosage amounts for a subject of from about 0.005 to about 500 mg/kg of body weight of active compound per day, which may be administered in a single dose or in the form of individual divided doses, such as from 1 to 4 times per day.

Alternatively, the dosage amount may be from about 0.01 to about 450 mg/kg of body weight of active compound per day, from about 0.05 to about 400 mg/kg of body weight of active compound per day, from about 0.1 to about 300 mg/kg of body weight of active compound per day, from about 0.1 to about 250 mg/kg of body weight of active compound per day, from about 0.2 to about 200 mg/kg of body weight of active compound per day, from about 0.5 to about 150 mg/kg of body weight of active compound per day, from about 0.5 to 100 mg/kg of body weight of active compound per day, from about 0.5 to about 75 mg/kg of body weight of active compound per day, from about 0.5 to about 50 mg/kg of body weight of active compound per day, from about 0.5 to about 25 mg/kg of body weight of active compound per day, from about 1 to about 20 mg/kg of body weight of active compound per day, from about 1 to about 15 mg/kg of body weight of active compound per day, from about 1 to about 10 mg/kg of body weight of active compound per day.

In specific embodiments, the dosage amount may be about 500 mg/kg of body weight of active compound per day, about 400 mg/kg of body weight of active compound per day, about 300 mg/kg of body weight of active compound per day, about 200 mg/kg of body weight of active compound per day, about 100 mg/kg of body weight of active compound per day, about 50 mg/kg of body weight of active compound per day, 20 mg/kg of body weight of active compound per day, about 10 mg/kg of body weight of active compound per day, about 5 mg/kg of body weight of active compound per day, about 1 mg/kg of body weight of active compound per day, about 0.5 mg/kg of body weight of active compound per day, or about 0.1 mg/kg of body weight of active compound per day.

In specific embodiments, the composition of the subject invention may be administered at least once a day, twice a day, or three times a day for consecutive days, e.g. 2, 3, 4, 5, 6, 7, 8, 9, 10, 11, 12, 13, 14, 15, 16, 17, 18, 19, 20, 21, 22, 23, 24, 25, 26, 27, 28, 29, or 30 days. The composition of the subject invention may also be administered for weeks, months or years.

As used herein, the singular forms "a," "an," and "the" are intended to include the plural forms as well, unless the context clearly indicates otherwise. Further, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof), such as "comprising," "comprises," and "comprise," can be used interchangeably.

The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of concentrations of ingredients where the term "about" is used, these values include a variation (error range) of 0-10% around the value (X±10%).

EXAMPLES

Experimental Section

Materials and Methods
Reagents

The SCREEN-WELL FDA approved drug library V2 was purchased from Enzo (Farmingdale, NY). All individual compounds were purchased from Sigma-Aldrich (St. Louis, MO). Nystatin (N4014), ceftazidime (CDS020667), calcipotriene (C4369) and prasugrel (SML0331) were all dissolved in sterile DMSO (MP Biomedicals, Solon, OH). Natamycin (P0440) is supplied as a 2.5% γ-irradiated saline solution. Oligonucleotides were from Integrated DNA Technologies (IDT, Coralville, IA). The oligonucleotide containing a BHQ-tagged T was from LGC Biosearch Technologies (Petaluma, CA). *E. coli* Exo III was from New England BioLabs (Ipswitch, MA). All chemical reagents were from Sigma-Aldrich (St Louis, MO) and Thermo Fisher Scientific Inc (Weston, FL).

High Throughput Screening Assay for Inhibitors of the BER Pathway

The high throughput screening assay was described in U.S. Pat. No. 9,809,843 B1. Briefly, a fluorescence-tagged oligonucleotide substrate that contains a synthesized abasic site, i.e., tetrahydrofuran (THF) was designed to determine the total capacity of BER in prostate cancer whole cell extracts.

The sequence of the oligonucleotides for constructing the substrate is:

```
SEQ ID NO: 1:
5'-CTGGA [FluorT]ACAC GAACT TTAAG CATHFAG

TCAAT GAAGG ACGCA TATCA GTG-3' (upper strand);
and

SEQ ID NO: 2:
5'-CACTG ATATG CGTCC TTCAT TGACT CTGCT TAAAG

TTCGT G[T(BHQ-1)]ATC CAG-3 (bottom strand).
```

A 6-carboxyfluorescein (6-FAM)-tagged-T is inserted upstream of the abasic site in the damaged strand and close to a black hole quencher (BHQ) tagged-T, which was inserted in the template strand (FIG. 1). The substrate was constructed by annealing the damaged strand with the template strand at 1:1 ratio. The substrate (25 nM) was precut with 25 or 50 nM purified human AP endonuclease 1 (APE1) at 37° C. for 30 min. Subsequently, the substrate was incubated with 25 μg prostate cancer cell extracts (total volume of 10 μL) at 37° C. for 30 min allowing repair of the abasic site by BER. Unrepaired substrates were then subject to digestion by the 3'-5' exonuclease activity of *E. coli* Exo III (0.5 U) (New England BioLabs, Ipswitch, MA) at 37° C. for 10 min. This cleaved the upstream strand in the unrepaired substrates releasing the 6-FAM-tagged T and allowing the emission of fluorescence detected by a fluorescence plate reader at 528±20 nm (Biotek Instruments, Winoski, VT). Inhibition of BER enzymatic activity and/or the coordination among BER enzymes and their cofactors reduced the amount of repaired products and led to the accumulation of unrepaired substrates thereby significantly increasing the intensity of fluorescence signal. The approach was used with a 384-well platform in high throughput screening for inhibitors of the BER pathway.

High Throughput Screening for BER Inhibitors

The Screen-Well® FDA Approved Drug Library V2 with 774 compounds was purchased from Enzo. The 10 mM stock solutions in DMSO were diluted to 2 mM before 0.5 μL was added to 10 μL of each assay reaction mixture of 50 mM Tris-HCl (pH 7.5), 50 mM KCl, 0.1 mM Ethylenediamine tetraacetic acid (EDTA), 0.1 mg/ml bovine serum albumin, 0.01% Nonidet P-40, 25 or 50 nM APE1 pre-cut substrate and cancer cell extract (72 μg of LNCaP cell lysate per assay) in 384-well black plates (Corning 3821), for a final compound concentration of 100 μM. The control reaction also has 5% DMSO added. After mixing for 2 min and spinning at 200 g for 1 min, the plates were incubated at 37° C. for 30 min. Freshly diluted Exo III (0.5 U, New England BioLabs) was then added for an additional incubation at 37° C. for 10 min, followed by 30 min at 50° C. The reactions were terminated by adding 1 μL of 500 mM EDTA. Fluorescence signal (excitation wavelength of 485±20 nm and emission wavelength of 528±20 nm) were recorded with the Biotek Synergy HT Plate Reader. Compounds that showed a signal greater than DMSO control+3 S.D for each plate were chosen as hits. Twenty-six hits were selected from 774 compounds (3.4%).

Secondary Assays of BER Inhibitors

The hit compounds were subject to secondary assays to determine their ability to reduce the BER capacity when reconstituted with purified core BER enzymes, as well as their inhibitory effects on individual BER enzymes including pol β, FEN1 and LIG I. The effect of hit compounds on BER capacity and BER enzymes was examined using a denaturing sequencing gel-based assay. 10 μM hit compounds were incubated with 10 nM pol β, 10 nM FEN1 and 20 nM LIG I in BER reaction buffer containing 50 mM Tris-HCl (pH 7.5), 50 mM KCl, 0.1 mM EDTA, 0.1 mg/ml bovine serum albumin, and 0.01% Nonidet P-40 in the presence of 5 mM $Mg^{2+}$ and 2 mM ATP. The compounds were initially preincubated with a BER enzyme at varying concentrations for 1 h with rotation. This was followed by the addition of 25 nM $^{32}$P-labeled substrate containing an abasic site, which was precut with 25 or 50 nM APE1. The reaction mixture (20 μL) was incubated at 37° C. for 30 min, and the reaction was terminated by 50 mM EDTA. Substrates, products, and unrepaired BER intermediates were separated by 15% urea-denaturing sequencing gel and detected by a Pharos FX Plus PhosphorImager (Bio-Rad, Hercules, CA).

Cell Culture

LNCaP, LAPC4, PNT1A, and RWPE1 cell lines were purchased from ATCC (Manassas, VA) and used within 8 passages after plating. LNCaP and PNT1A and were maintained in RPMI-1640 supplemented with 10% FBS 1% PenStrep. LAPC4 were maintained in RPMI-1640 supplemented with 10% FBS, 1% PenStrep and $10^{-8}$M of R1881. RWPE1 was maintained in Keratinocyte-SFM supplemented with EGF and BPE, according to ATCC guidelines. All media and PenStrep were purchased from Gibco (Carlsbad, CA). FBS and charcoal stripped serum were purchased from Sigma-Aldrich (St. Louis, MO). Charcoal stripped Serum (CSS) was purchased from HyClone (Logan, UT). R1881 was purchased from Perkin Elmer (Waltham, MA).

Proliferation Assay

Proliferation assays were done using Roche DP Real Time Cell Analyzer (RTCA), as described by the manufacturer. Background impedance was established after incubating E-plates (Acea Biosciences, San Diego, CA) with 50 μL media at room temperature for 30 min and placed in RTCA. Cells were then seeded in 100 μL per well. Cells attached overnight and then treated. During attachment stage and after treatment impedance was measured every 30 min. Impedance is represented by cell index and is calculated as follows: $CI=(Z_i-Z_o)/15\Omega$ where $Z_i$ is impedance at an individual time point, and $Z_o$ is the background impedance. Average CI was calculated from four wells per treatment at each time point and normalized to the impedance immediately after compound addition. All data was normalized to the impedance at the time of treatment, which was assigned a value of 1.

Viability Assay

Cell viability was determined using the Cell Titer Glo Cell Viability Assay (Promega, Madison, WI), as recommended by manufacturer. All experiments were performed in quadruplicate.

Toxicity Assay

Cellular toxicity was assessed using the MTT assay. Cells were seeded in a 96 well plate at $1\times10^4$ cells/well and allowed to adhere overnight in the presence of FBS or CSS. The following day treatment was added to the wells and the plates were incubated for 24 h or 48 h. After incubation, 50 μL of MTT (2 mg/mL) was added to each well and incubated in the dark for 4 h. After incubation 150 μL of the media/MTT solution was removed and 100 μL of DMSO was added to each well and incubated for 15 min. Absorbance at 570 nm was measured using a ClarioStar Plate Reader (BMG LabTech, Ortenburg, Germany).

Western Blotting

Whole cell lysate protein was extracted with protein extraction buffer [20 mM Tris, 150 mM NaCl, 1 mM EDTA, 1% Triton-X] supplemented with protease inhibitors (GenDepot, Barker, TX). For each sample 20 μg of protein was resolved on a 10% sodium dodecyl sulfate-polyacrylamide gel electrophoresis (SDS-PAGE) and transferred to a Polyvinylidene difluoride (PVDF) membrane (GE Healthcare, Germany). Immunoblotting was done using primary antibodies for Tubulin (1:5000; Millipore, Temecula, CA), γ-H2A.X [Ser139] (1:1000; Cell Signaling, Danvers, MA), and AR (1:1000; Santa Cruz, Dallas, TX). Chemiluminescent signal was captured using an ImageQuant LAS 500 (GE Healthcare, Uppsala, Sweden).

Measurement of the Inhibitory Effects of Natamycin on Pol □ DNA Synthesis and LIG I Activity The inhibitory activities of natamycin on pol β DNA synthesis were measured by incubating the substrates containing 1-nt gap (50 nM) with 5 nM pol β in the presence of 1, 2, 5 or 10 μM natamycin in BER reaction buffer (50 mM Tris-HCl, pH 7.5, 50 mM KCl, 0.1 mM EDTA, 0.1 mg/ml bovine serum albumin, and 0.01% Nonidet P-40) with 5 mM $MgCl_2$ and 50 μM dNTPs. The inhibitory activities of natamycin on LIG I (5 nM) activity were tested on the substrate containing random DNA sequence with a nick in BER reaction buffer with 5 mM $MgCl_2$ and 2 mM ATP in the presence of 0.1, 0.5, 1 or 5 μM natamycin. Reaction mixtures were assembled on ice and incubated at 37° C. for 15 min. BER reactions were terminated by adding 2× stopping buffer containing 95% formamide and 10 mM EDTA. Reaction mixtures were then denatured at 95° C. for 5 min and separated by 15% urea-denaturing polyacrylamide gel electrophoresis. Substrates and products were detected and analyzed using a Pharos FX Plus PhosphorImager (Bio-Rad, Hercules, CA). For all the reactions, natamycin was preincubated with the BER enzymes for 2 h at 4° C. with rotation.

Example 1—Primary Screening of Compounds that Inhibit the BER Pathway

To identify FDA approved compounds that can directly inhibit the activities of BER enzymes and co-factors, a high throughput, BER pathway—specific screening approach was developed (FIG. 1). This method was used to identify compounds that interfere with the interactions between BER enzymes and co-factors in cancer cells, e.g., the prostate cancer cell line LNCaP. This technique relies on the design of an oligonucleotide substrate with a fluorescent 6-FAM labeled abasic lesion located adjacent to a black quencher (BHQ) in the template strand. Efficient BER of the abasic lesion will lead to quenching of the 6-FAM fluorescent tag, whereas inhibition of BER will spatially separate 6-FAM and BHQ tags increasing fluorescent signal (FIG. 1). Using this approach, a high throughput screening of 774 compounds was performed from the Screen-Well® FDA Approved Drug Library V2, in LNCaP cell lysates. The initial screen identified 26 compounds that exerted significant inhibition on BER as indicated by a more than 3-fold increase in fluorescent signal over the background.

Figure 2:
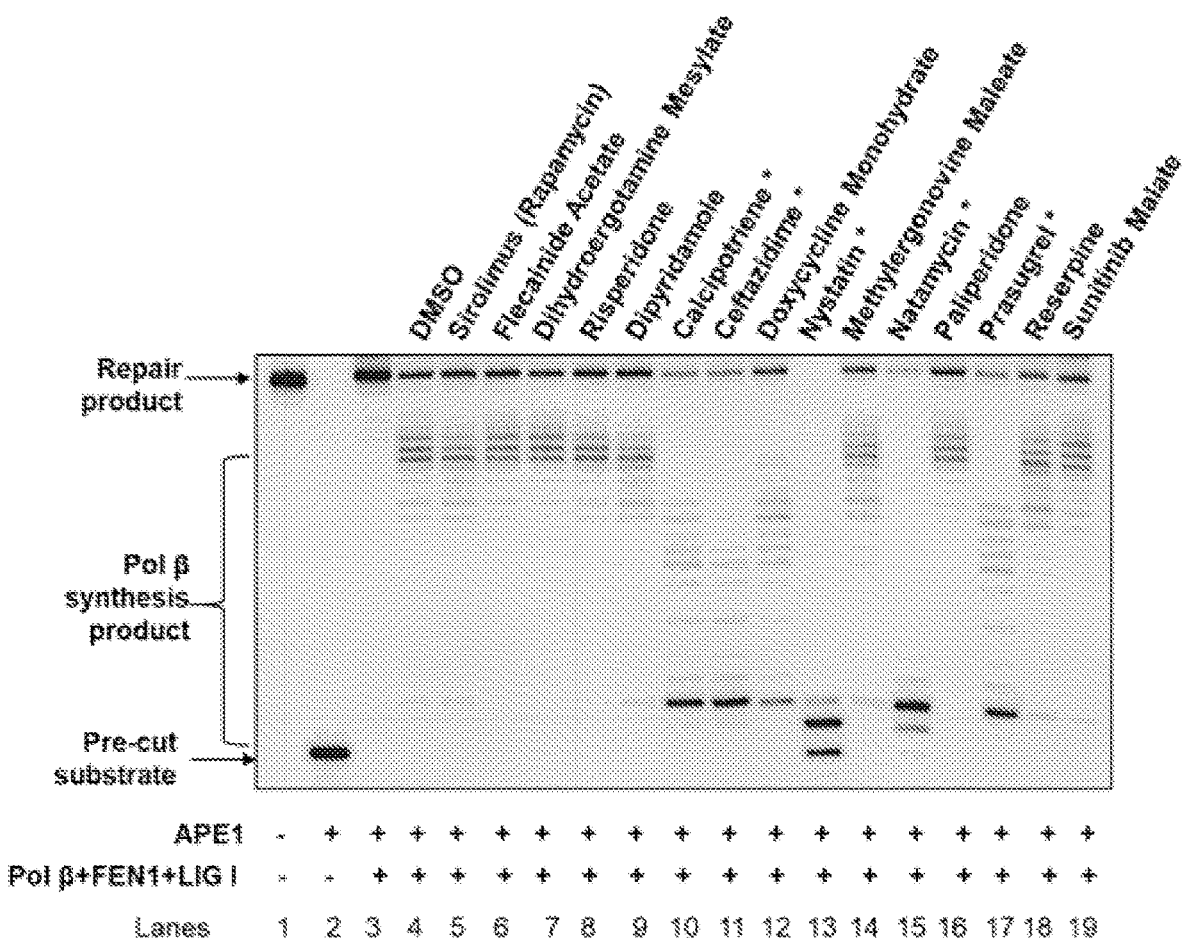
FIG. 2 shows a secondary screen of BER inhibitors. The secondary screening assay was performed as described below in the "Materials and Methods" section. Lane 1 represents the substrate only. Lane 2 indicates the reaction mixture with 5 nM APE1. Lanes 3 and 4 correspond to the reaction mixture with 5 nM APE1, 10 nM pol β, 10 nM FEN1 and 20 nM LIG I in the absence and presence of dimethylsulfoxide (DMSO). Lanes 5 through 19 correspond to the reaction mixture with 5 nM APE1, 10 nM pol β, 10 nM FEN1 and 20 nM LIG I in the presence of indicated compounds. The experiments were repeated at least three times. A representative gel is illustrated. "*" denotes the hit compounds that exhibited significant BER capacity inhibitory effects in the secondary screening assay.

Example 2—Secondary Screening of Compounds that Inhibit the Activities of BER Enzymes Among the 26 identified compounds, nine were DNA intercalators or inhibitors of human DNA topoisomerases and were excluded from further studies. Thus, fifteen FDA approved drugs were selected for further testing. To further confirm the inhibitory effects of the lead compounds on BER, the effects of the compounds on BER reactions reconstituted with purified BER core enzymes were initially determined. The substrate containing the abasic site analogue THF was reconstituted with purified Pol β, FEN1, and LIG I. The results demonstrated that 5 compounds, calcipotriene, ceftazidime, nystatin, natamycin and prasugrel (FIG. 2, marked*) significantly reduced BER capacity and the production of the BER repair product, suggesting that the compounds inhibited BER by inhibiting the activities of the BER core enzymes.

Figure 3A:
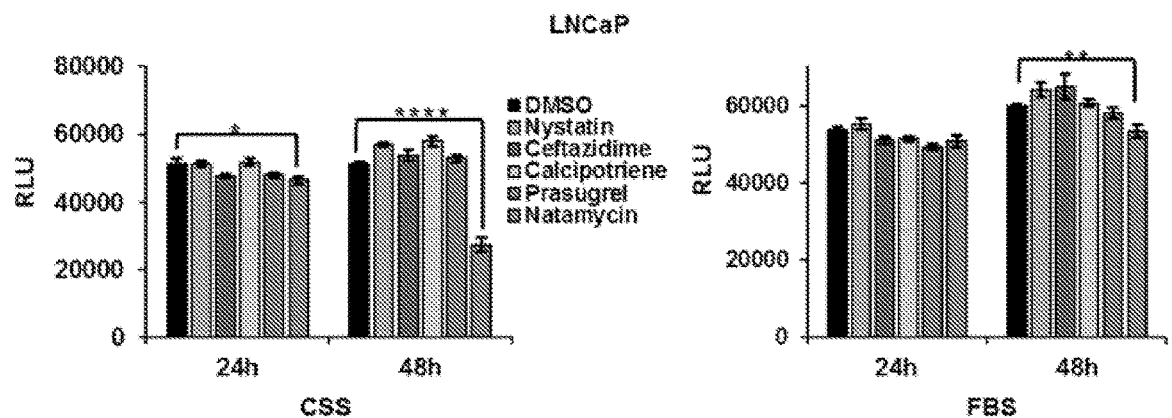
FIGS. 3A-3B show cellular toxicity of the lead compounds in androgen-dependent prostate cancer cell lines. (3A) LNCaP cells were plated in a 96-well plate at $1 \times 10^4$ cells/well in the presence of Fetal Bovine Serum (FBS) or Charcoal stripped Serum (CSS). Cells were allowed to attach overnight and were treated with either vehicle (DMSO) or 10 µM of indicated compound. At 24 and 48 h cellular viability was compared using the Cell Titer Glo Luminescent Cell Viability kit. (3B) LAPC4 cells were plated in a 96-well plate at a density of $1 \times 10^4$ cells/well in the presence of FBS or CSS. Cells were allowed to attach overnight and treated with 10 µM of indicated compound. At 24 h and 48 h cellular viability was compared as in A. (* signifies a difference between vehicle and treatment with *p≤0.05, p≤0.01, *p≤0.001 ****p≤0.0001).
Figure 3B:
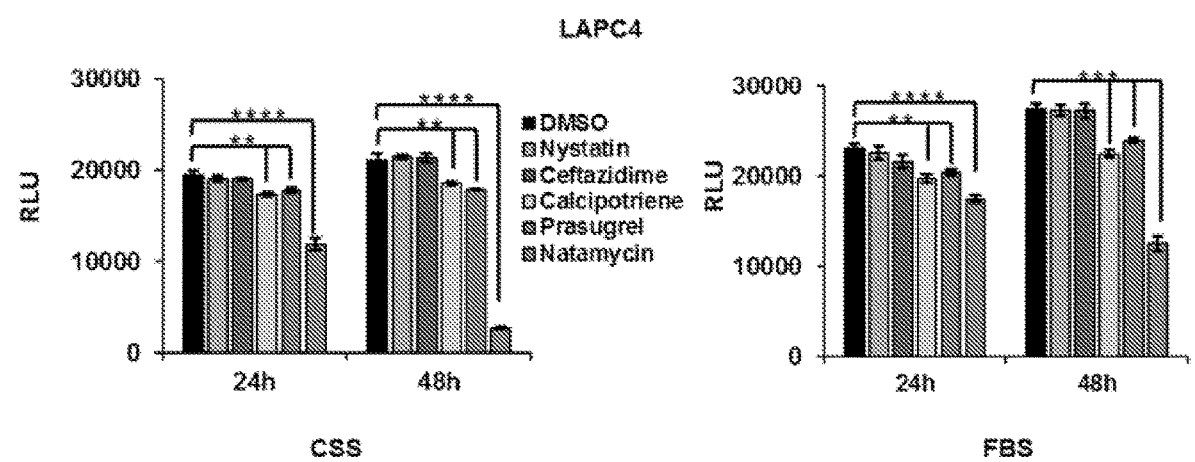

Example 3—Validation of Inhibitory Effects of the Lead Compounds on the Proliferation of Malignant and Non-Malignant Prostate Cell Lines To determine whether lead BER inhibitors affect cell survival, the independently derived androgen-dependent prostate cancer cells, LNCaP and LAPC4, were treated with vehicle (DMSO) or 10 μM nystatin, ceftazidime, calcipotriene, prasugrel, or natamycin. The highest toxicity was observed in prostate cancer cells maintained in androgen depleted conditions treated with natamycin (FIGS. 3A-B).

Figure 4A:
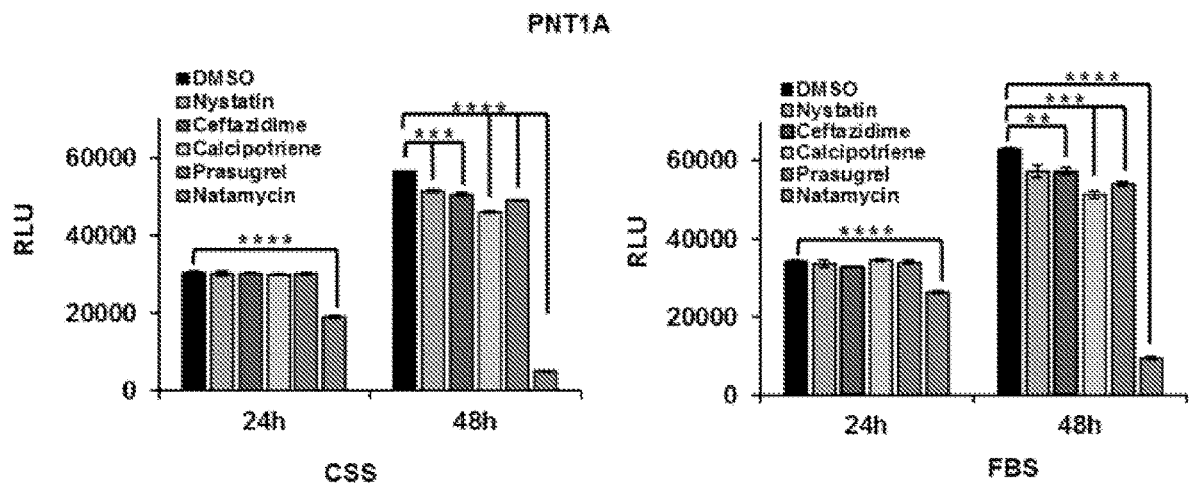
FIGS. 4A-4B show cellular toxicity of lead compounds in nonmalignant androgen independent prostate-derived cell lines. (4A) PNT1A cells were plated in a 96-well plate at $1 \times 10^4$ cell/well in the presence of FBS or CSS. Cells were allowed to attach overnight and were treated with either vehicle (DMSO) or 10 µM of indicated compound. At 24 and 48 h, cellular viability was compared using the Cell Titer Glo Luminescent Cell Viability kit. (4B) RWPE1 cells were plated in a 96-well plate at $1 \times 10^4$ cells/well using the specified serum free media. Cells were allowed to attach overnight and treated with 10 µM of indicated compound. At 24 h and 48 h, cellular viability was compared as in A. (* signifies a difference between vehicle and treatment with p≤0.01, *p≤0.001, ****p≤0.0001)
Figure 4B:
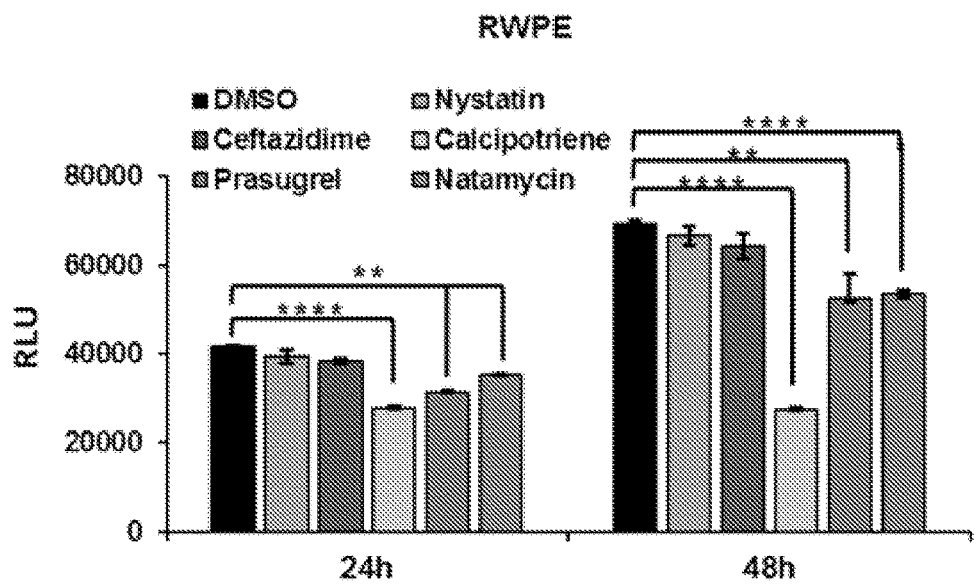

Next, whether the same concentration of compounds decreases the viability of the AR negative and nonmalignant prostate derived cells, PNT1A and RWPE1, was tested. In PNT1A, natamycin displayed similar toxicity in both FBS and CSS supplemented medium (FIG. 4A). Medium for RWPE1 cell lines does not include serum, rather it contains the growth hormone supplements, Epidermal Growth Factor (EGF) and Bovine Pituitary Extract (BPE). Calcipotriene, prasugrel, and natamycin significantly decreased RWPE1 cell viability at 10 μM after 24 h and 48 h (FIG. 4B). Thus, androgen depletion significantly and specifically enhances natamycin toxicity in androgen dependent prostate cancer cell lines.

Figure 5A:
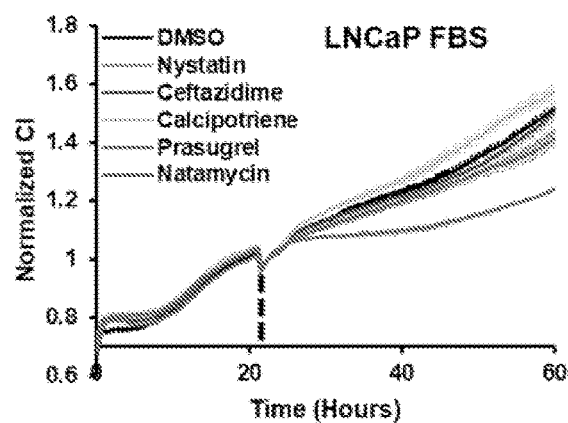
FIGS. 5A-5D show that natamycin suppresses cellular proliferation and adhesion in androgen dependent prostate cancer cell lines. (5A-5B) LNCaP cells were plated onto xCelligence E-plates at $10^4$ cells per well in medium supplemented with either 10% FBS (5A) or 10% CSS (5B) serum. Cells attached overnight and were treated with vehicle (DMSO) or 10 µM of the indicated compounds. (5C-5D) LAPC4 cells were plated at $5 \times 10^4$ cells per well onto xCelligence E-plates in media supplemented with FBS (5C) or CSS (5D) and allowed to attach overnight. Treatment was conducted as in (5A-5B) and impedance measured continuously in 30 min intervals. Impedance in all graphs was normalized to the time of treatment, which was assigned a value of 1.
Figure 5B:
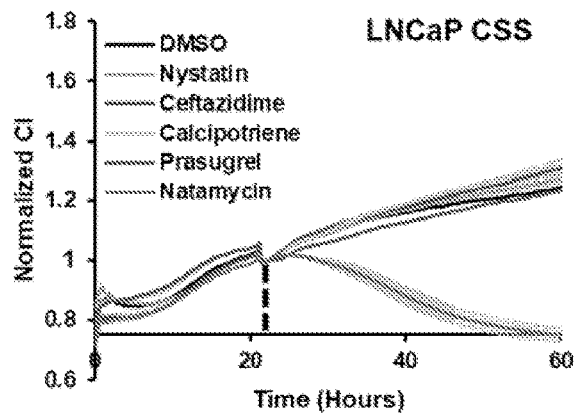
Figure 5C:
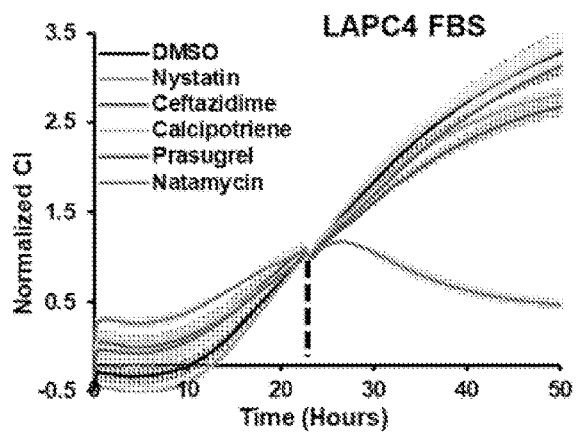
Figure 5D:
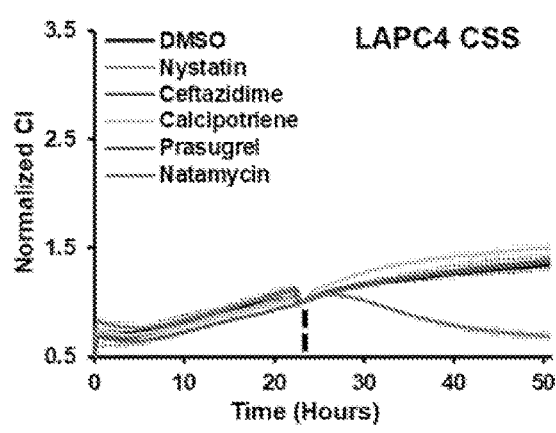

The effects of 10 μM nystatin, ceftazidime, calcipotriene, prasugrel, or natamycin on cellular proliferation in LNCaP, LAPC4, PNT1A, and RWPE1 cell lines were then compared. As seen in FIG. 5A, in the presence of FBS, LNCaP cells were able to proliferate in the presence of all inhibitors. However, natamycin-treated cells had the slowest proliferation rate (FIG. 5A). Consistent with previous reports, LNCaP cells proliferated more slowly in androgen depleted medium and addition of 10 µM natamycin abolished cellular impedance (FIG. 5B), suggesting cell detachment. In LAPC4 cells, cellular proliferation and attachment was abolished after treatment with 10 µM natamycin in medium supplemented with both FBS (FIG. 5C) and CSS (FIG. 5D).

Figure 6A:
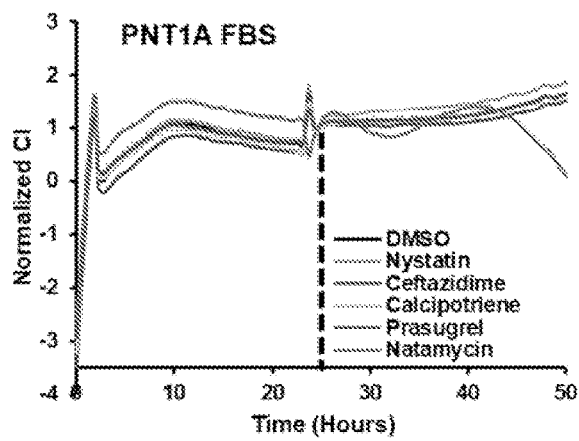
FIGS. 6A-6C show that androgen-independent prostate derived cell lines are sensitive to high concentrations of natamycin. (6A-6B) PNT1A cells were plated onto xCelligence E-plates at $5 \times 10^4$ cells per well in media supplemented with 10% FBS (6A) or CSS (6B). Cells were allowed to attach overnight and treated with vehicle (DMSO) or 10 µM of indicated compounds. Cellular impedance was monitored continuously with 30 min intervals. (6C) RWPE1 cells were plated at $5 \times 10^4$ cells per well in serum free medium supplemented with Epidermal Growth Factor (EGF) and Bovine Pituitary Extract (BGP) onto E-plates and treated with 10 µM of indicated compounds as indicated. Impedance was continuously measured using Roche DP Real Time Cell Analyzer (RTCA) every 30 min and was normalized to the time of treatment which was assigned a value of 1.
Figure 6B:
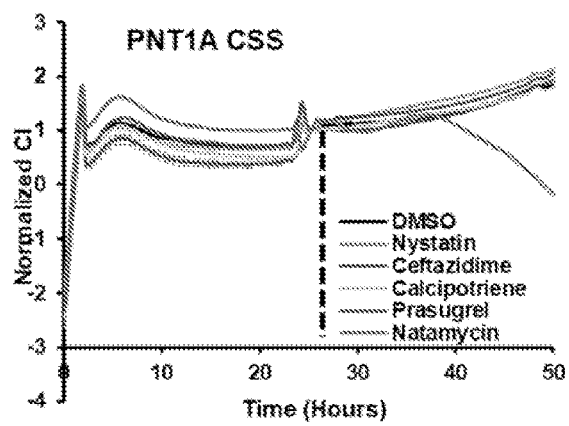
Figure 6C:
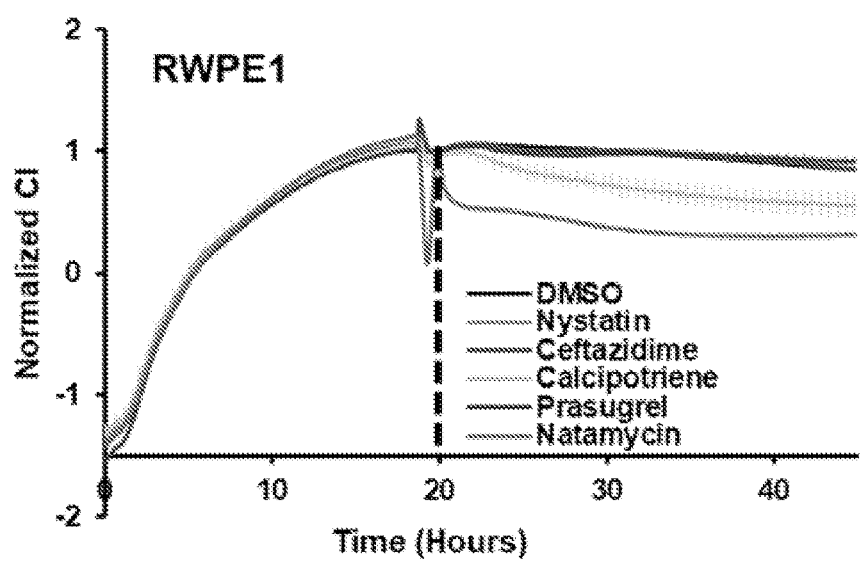

The nonmalignant, AR negative cell line PNT1A proliferated in the presence of all inhibitors except natamycin, in both FBS (FIG. 6A) and CSS supplemented media (FIG. 6B). However, natamycin effect became evident only at 42 h of treatment. RWPE1 was slightly inhibited by 10 µM natamycin and calcipotriene (FIG. 6C). Both cell lines remained attached after treatment with all inhibitors.

To determine whether AR positive and AR negative cell lines have different sensitivity to natamycin, LNCaP and PNT1A were treated with 10 µM, 1 µM, and 0.1 µM of the compound. LNCaP cell proliferation was significantly inhibited by all concentrations in FBS medium (FIG. 7A) and 10 µM and 1 µM were inhibitory in medium with CSS (FIG. 7B). PNT1A cell proliferation was inhibited only with 10 µM natamycin in both CSS (FIG. 7C) and FBS (not shown) medium. In LNCaP cells, natamycin reduced viability preferentially in androgen-depleted conditions. As seen in FIG. 7D, natamycin reduced the viability of LNCaP cells in CSS medium at concentrations of 0.1 µM and higher, while treatment with 2.5 µM or higher concentration was required to reduce LNCaP viability in medium supplemented with FBS.

Figure 7E:
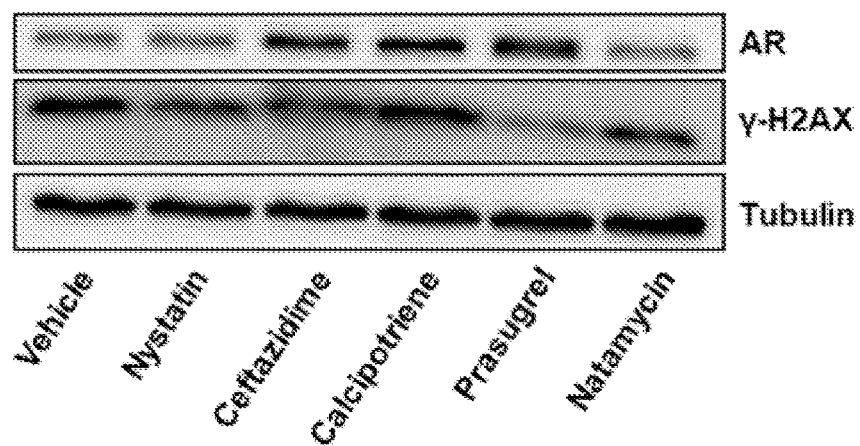

The proliferation of androgen dependent cell lines is driven in part by AR signaling. To test whether these compounds affect AR signaling, AR protein levels were compared after 48-hour treatment with 10 µM of each compound. As seen in FIG. 7E, natamycin slightly decreased AR levels, while no decline was observed with other compounds. No significant increase in the marker of double-stranded breaks, $\gamma$-H2AX, was evident at 48 h after treatment with the indicated inhibitors.

Example 4—the Inhibitory Effects of Natamycin on BER Enzymes

Figure 8A:
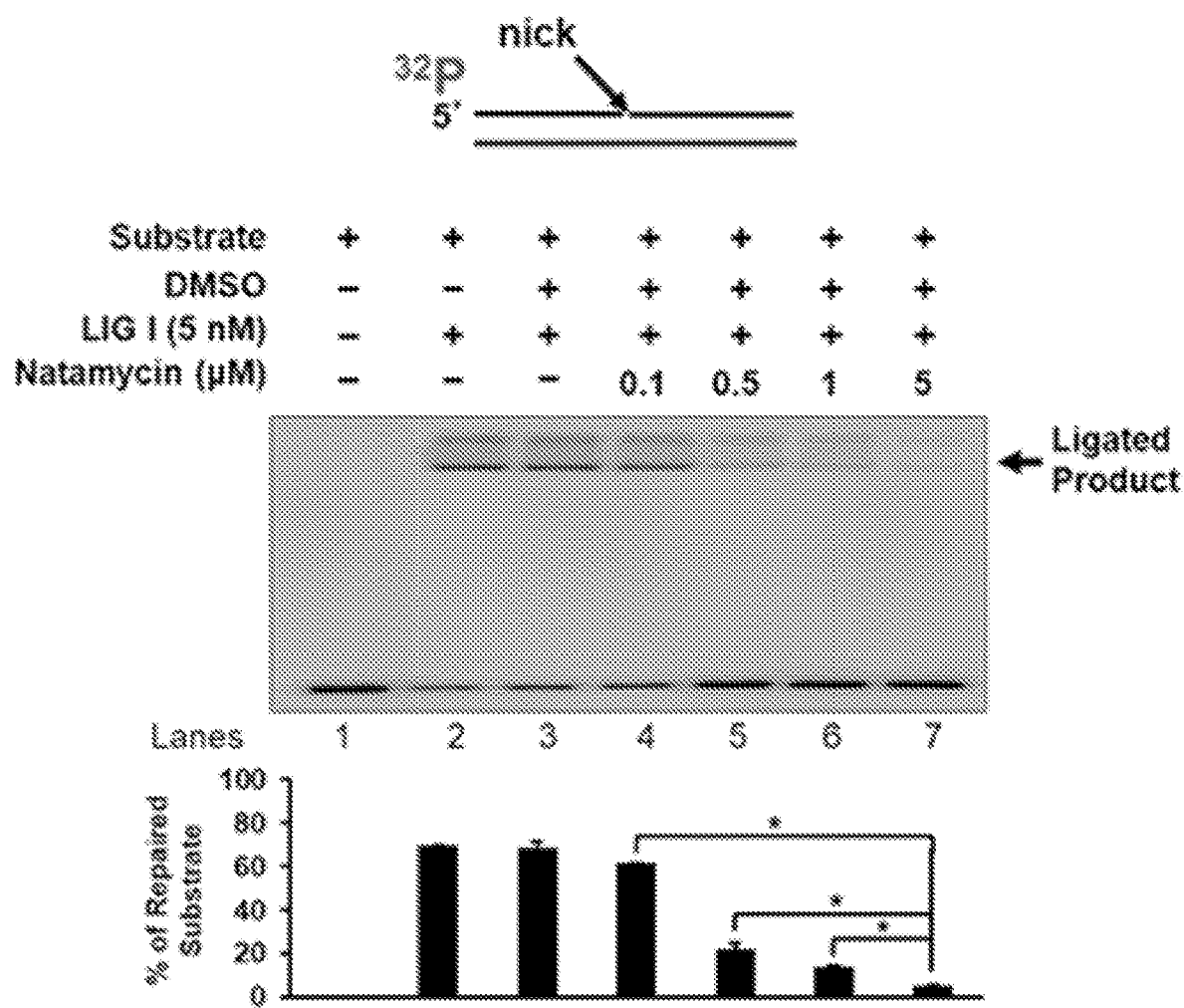
FIGS. 8A-8B show that natamycin inhibits BER enzymes pol β and LIG I. (8A) The inhibitory effect of natamycin on LIG I activity was examined with the substrate containing a nick. Lane 1 represents the substrate only. Lanes 2 and 3 indicates the reaction mixture with 5 nM LIG I in the absence and presence of DMSO. Lanes 4-7 correspond to the reaction mixture with 5 nM LIG I in the presence of increasing concentrations of natamycin. The substrate was $^{32}$P-labeled at the 5'-end of the upstream strand and is illustrated above the gel. The experiments were repeated at least three times. Representative gel is illustrated. Quantification of the results is shown below the gel. Two-way ANOVA with Tukey's multiple comparison posttests was used to determine statistically significant differences. * signifies p<0.05 compared to the control reaction with LIG I and DMSO. It should be noted that the upper band is the smearing of the ligated products in the course of gel electrophoresis. (8B) The inhibitory effect of natamycin on pol β DNA synthesis was determined with the substrate containing a 1-nt gap as described below in the "Materials and Methods" section. Lane 1 represents the substrate only. Lanes 2 and 3 indicates the reaction mixture with 5 nM pol β in the absence and presence of DMSO. Lanes 4-7 correspond to the reaction mixture with 5 nM pol β in the presence of increasing concentrations of natamycin. The substrate was $^{32}$P-labeled at the 5'-end of the upstream strand and is illustrated above the gel. The experiments were repeated at least three times. Quantification of the results are shown below the gel. Two-way ANOVA with Tukey's multiple comparison posttests was used to determine statistical significance. * signifies p<0.05 compared to the control reaction with pol β and DMSO.
Figure 8B:
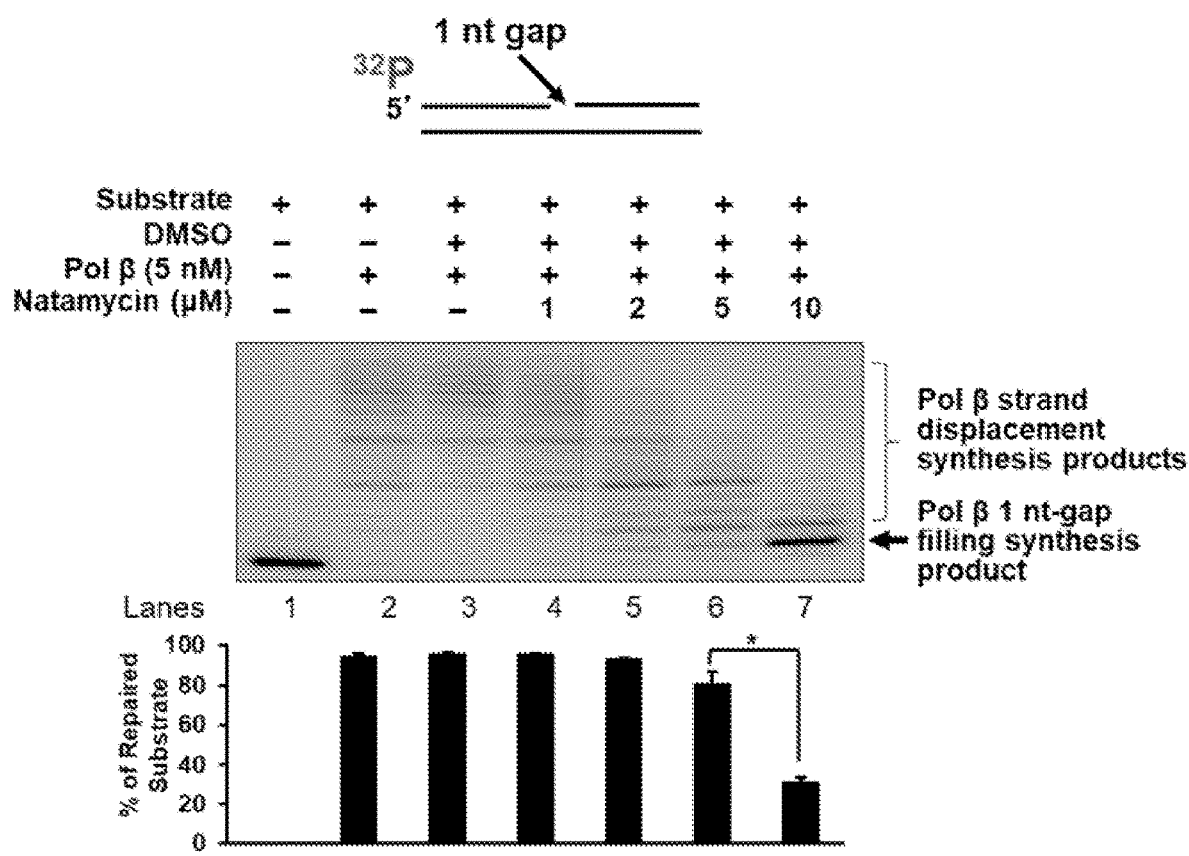

To further determine if natamycin reduced BER capacity by inhibiting a specific BER enzyme, the inhibitory effects of natamycin on the activities of the core BER enzymes, LIG I, FEN1, and pol β was examined. At 0.5 µM and 1 µM, natamycin reduced the activity of LIG I by 3.5-fold (FIG. 8A). At 5 µM, it decreased the activity of LIG I by 14-fold (FIG. 8A). Natamycin showed a significantly milder inhibitory effect on pol β at low concentrations. At 10 µM natamycin reduced pol β activity by 3-fold (FIG. 8B). Moreover, the results showed that natamycin exhibited a significant inhibitory effect on pol β strand-displacement synthesis at 2 nM-5 nM but did not inhibit pol β 1 nt gap-filling synthesis (FIG. 8B, lanes 5-7) further indicating that natamycin specifically inhibited long-patch BER rather than SN-BER. No inhibitory effect of natamycin on FEN1 was detected. The results indicate that natamycin moderately inhibited pol β DNA synthesis activity and exhibited a potent inhibition on LIG I activity. The results further indicate that natamycin reduced the BER capacity of prostate cancer cells primarily by inhibiting the activity of LIG I along with the moderate inhibition the strand-displacement synthesis of pol β. This further suggests that natamycin can lead to the accumulation of single-strand DNA breaks in prostate cancer cells, impeding cell proliferation.

It has been found that the steady state levels of LIG I are elevated in cancer cell lines compared to normal cells, presumably due to the necessity of this enzyme for the aggressive proliferative activity of cancer cells. Thus, the development of ligase inhibitors may potentiate the toxic effects of chemotherapeutic agents used for cancer treatment.

As the central component of BER, pol β plays a significant role in the drug resistance of cancer therapy due to its "translesion" DNA synthesis that can help cancer cells tolerate DNA damage caused by some anticancer therapies. Pol β is mutated in approximately 30% of tumors leading to a reduction in pol β fidelity during DNA synthesis and promoting mutagenesis and survival of the tumor cells. Thus, targeting pol β has been considered as a promising therapeutic strategy for the improvement of cancer treatment.

Inhibition of pol β DNA synthesis can result in the accumulation of gapped DNA intermediates that cannot be ligated by DNA ligases, suggesting that the synergy between the inhibition of LIG I and pol β by natamycin may sensitize prostate cancer cells to endogenous cancer-specific DNA damage as well as DNA damaging and hormonal cancer therapies.

Example 5—Anti-Prostate Cancer Treatment In Vivo Using Animal Models

Animal models are utilized to further advance the discovery of natamycin towards its use for clinical treatment of CRPC patients. Natamycin kills cancer cells while sparing benign cells in a whole body milieu.

To determine whether natamycin differentially affects cancer and normal tissues, human cell line xenograft model of prostate cancer is used. Human prostate cancer cell line LAPC4 is used to implant into immunocompromised NOD scid male mice. Once tumor sizes reach 0.5 cm$^3$, the mice are separated into two groups. First group is treated with natamycin and the second group with vehicle control intravenously for an additional 4 weeks. During this time, tumor size in each mouse is monitored to determine whether tumor growth is suppressed by the natamycin treatment. At the end of the 4-week treatment, mice are euthanized. Their tumors are excised and weighed. Tumors, samples of adjacent nonmalignant tissues, and prostates are collected for comparative analysis.

Histopathological evaluation of prostate cancer xenograft and mouse prostate are conducted to determine whether natamycin kills cancer cells while sparing nonmalignant prostate tissues. The cellular proliferation and cell death in cancerous, adjacent benign, and normal mouse prostate tissues in control and natamycin treated animals are scored.

Expressions of genes that are markers of proliferation and of cell death are compared to evaluate changes in prostate cancer viability caused by natamycin treatment. A portion of the tumor is used for RNA-Seq (RNA sequencing) analysis to reveal the presence and quantity of the entire set of RNA present in these cells. The RNA-Seq results provide mechanistic insight into mechanisms of natamycin action in prostate cancer cells. A section of tumors treated with vehicle and natamycin, respectively, along with adjacent nonmalignant tissues, and other vulnerable tissues (liver, white blood cells, intestine, heart, and brain) is compared to determine the extent of DNA damage and repair following 4 weeks of natamycin treatment.

The impact of natamycin on DNA damage and repair capacity in prostate cancer xenograft tissue is measured. These measurements are performed using a fluorescence-based in situ DNA damage and repair assay. These measurements also provide new information about potency and efficacy of natamycin in prostate cancer treatment.

These findings demonstrate how DNA damage and DNA repair may be used as novel biomarkers for the new treatment of prostate cancer with natamycin. Natamycin treatment results in an overload of DNA damage that surpasses the capacity of DNA repair in prostate cancer tissue. DNA damage and repair capacity serve as sensitive biomarkers for the efficacy and prognosis of natamycin treatment of prostate cancer. Thus, natamycin has specific toxicity for prostate cancer cells while being well-tolerated by noncancerous tissues in a mouse model.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

---

---

We claim:

1. A method for inhibiting/reducing base excision repair (BER) capacity in a cancer cell comprising contacting the cancer cell with a composition comprising one or more compounds selected from natamycin, calcipotriene, ceftazidime, nystatin, prasugrel, sirolimus, flecainide acetate, dihydroergotamine mesylate, risperidone, dipyridamole, doxycycline monohydrate, methylergonovine maleate, paliperidone, reserpine, and sunitinib malate; and detecting an inhibitory effect on BER capacity in the cancer cell.

2. The method of claim 1, the cancer cell being a prostate cancer cell.

3. The method of claim 2, the prostate cancer cell being selected from organ-confined primary prostate cancer cells, locally invasive advanced prostate cancer cells, metastatic prostate cancer cells, and castration-resistant prostate cancer (CRPC) cells.

4. The method of claim 3, the prostate cancer cell being a CRPC cell.

5. The method of claim 1, the composition comprising natamycin.

6. The method of claim 1, the composition comprising one or more compounds selected from natamycin, calcipotriene, ceftazidime, nystatin, and prasugrel.

7. The method of claim 1, the composition further comprising an antiandrogen agent.

8. The method of claim 1, the inhibition/reduction of BER capacity within the cancer cell being through the inhibition of DNA Ligase I (LIG I) and DNA polymerase β (pol β).

9. A method for inhibiting/reducing base excision repair (BER) capacity in prostate cancer comprising administering to a subject having prostate cancer an effective amount of a pharmaceutical composition comprising one or more compounds selected from natamycin, calcipotriene, ceftazidime, nystatin, prasugrel, sirolimus, flecainide acetate, dihydroergotamine mesylate, risperidone, dipyridamole, doxycycline monohydrate, methylergonovine maleate, paliperidone, reserpine, and sunitinib malate; and detecting an inhibitory effect on BER capacity.

10. The method of claim 9, the prostate cancer being organ-confined primary prostate cancer, locally invasive advanced prostate cancer, metastatic prostate cancer, or castration-resistant prostate cancer (CRPC).

11. The method of claim 10, the prostate cancer being CRPC.

12. The method of claim 9, the composition comprising natamycin.

13. The method of claim 9, the composition comprising one or more compounds selected from natamycin, calcipotriene, ceftazidime, nystatin, and prasugrel.

14. The method of claim 9, the composition further comprising an antiandrogen agent.

15. The method of claim 9, the inhibition/reduction of BER capacity being through the inhibition of DNA Ligase I (LIG I) and DNA polymerase β (pol β).

16. The method of claim 9, the administration being local, oral, transdermal, parenteral, intracranial, intracerebral, intraspinal, intrauterine, or rectal administration.

17. The method of claim 1, the composition comprising one or more compounds selected from prasugrel, sirolimus, flecainide acetate, dihydroergotamine mesylate, risperidone, dipyridamole, doxycycline monohydrate, methylergonovine maleate, paliperidone, reserpine, and sunitinib malate.

18. The method of claim 9, the pharmaceutical composition comprising one or more compounds selected from prasugrel, sirolimus, flecainide acetate, dihydroergotamine mesylate, risperidone, dipyridamole, doxycycline monohydrate, methylergonovine maleate, paliperidone, reserpine, and sunitinib malate.

* * * * *